United States Patent
deCecco et al.

(10) Patent No.: US 7,884,321 B2
(45) Date of Patent: Feb. 8, 2011

(54) METHOD AND SYSTEM FOR NON-DESTRUCTIVE DISTRIBUTION PROFILING OF AN ELEMENT IN A FILM

(75) Inventors: Paola deCecco, Foster City, CA (US); Bruno Schueler, San Jose, CA (US); David Reed, Belmont, CA (US); Michael Kwan, Sunnyvale, CA (US); David Stephen Ballance, Cupertino, CA (US)

(73) Assignee: Revera, Incorporated, Sunnyvale, CA (US)

( * ) Notice: Subject to any disclaimer, the term of this patent is extended or adjusted under 35 U.S.C. 154(b) by 217 days.

(21) Appl. No.: 12/220,645

(22) Filed: Jul. 25, 2008

(65) Prior Publication Data

US 2008/0283743 A1 Nov. 20, 2008

Related U.S. Application Data

(62) Division of application No. 11/218,114, filed on Aug. 31, 2005, now Pat. No. 7,411,188.

(60) Provisional application No. 60/698,367, filed on Jul. 11, 2005.

(51) Int. Cl.
*H01J 37/26* (2006.01)

(52) U.S. Cl. ...................................... 250/305

(58) Field of Classification Search .................. 250/305, 250/306, 307, 310
See application file for complete search history.

(56) References Cited

U.S. PATENT DOCUMENTS

| 3,766,381 A | 10/1973 | Watson |
| 3,772,522 A | 11/1973 | Hammond et al. |
| 3,805,068 A | 4/1974 | Lee |
| 4,048,498 A | 9/1977 | Gerlach et al. |
| 4,810,880 A | 3/1989 | Gerlach |
| 5,315,113 A | 5/1994 | Larson et al. |
| 5,714,757 A | 2/1998 | Itabashi et al. |
| 6,122,042 A | 9/2000 | Wunderman et al. |
| 6,201,241 B1 | 3/2001 | Koike |

(Continued)

FOREIGN PATENT DOCUMENTS

JP  2005/071858  3/2005

OTHER PUBLICATIONS

First Office Action from Chinese Patent Application No. 2006/80033273.X mailed Apr. 6, 2010, 8 pgs.

(Continued)

*Primary Examiner*—Kiet T Nguyen
(74) *Attorney, Agent, or Firm*—Blakely, Sokoloff, Taylor & Zafman LLP

(57) ABSTRACT

A method to determine a distribution profile of an element in a film. The method comprises exciting an electron energy of an element deposited in a first film, obtaining a first spectrum associating with the electron energy, and removing a background spectrum from the first spectrum. Removing the background value generates a processed spectrum. The method further includes matching the processed spectrum to a simulated spectrum with a known simulated distribution profile for the element in a film comparable to the first film. A distribution profile is obtained for the element in the first film based on the matching of the processed spectrum to a simulated spectrum selected from the set of simulated spectra.

4 Claims, 16 Drawing Sheets

U.S. PATENT DOCUMENTS

| | | | |
|---|---|---|---|
| 6,399,944 B1 * | 6/2002 | Vasilyev et al. | 250/310 |
| 6,703,613 B2 | 3/2004 | Kaji et al. | |
| 6,800,852 B2 | 10/2004 | Larson et al. | |
| 6,891,158 B2 | 5/2005 | Larson et al. | |
| 6,930,306 B2 | 8/2005 | Kaji et al. | |
| 7,067,805 B2 | 6/2006 | Kaji et al. | |
| 7,250,601 B2 | 7/2007 | Kaji et al. | |
| 7,420,163 B2 * | 9/2008 | Schueler | 250/305 |
| 2004/0186383 A1 | 9/2004 | Rava et al. | |

OTHER PUBLICATIONS

International Search Report and Written Opinion from PCT/US2006/24581 mailed Apr. 30, 2008, 15 pgs.

International Preliminary Report on Patentability from PCT/US2006/24581 mailed Mar. 19, 2009, 10 pgs.

* cited by examiner

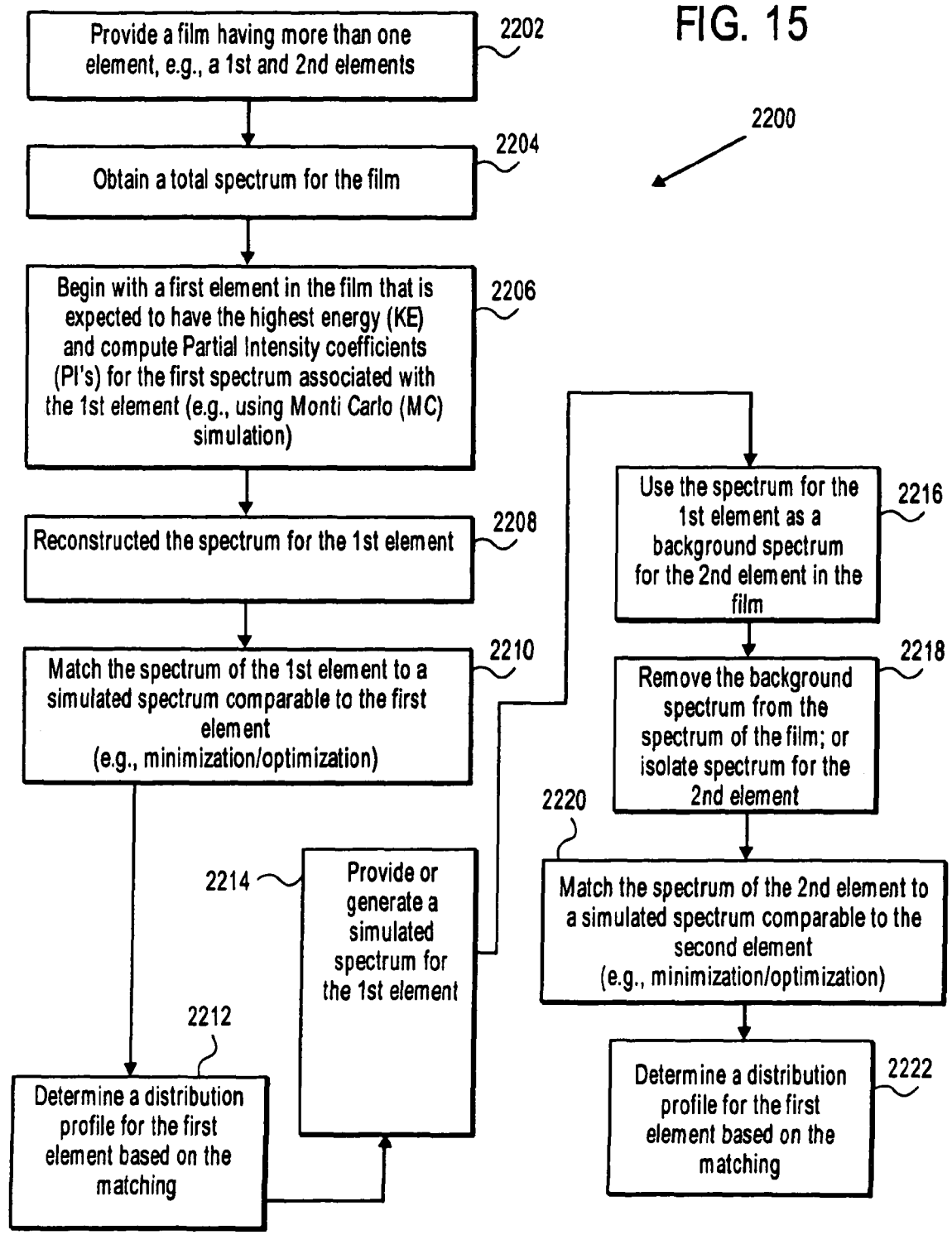

METHOD AND SYSTEM FOR NON-DESTRUCTIVE DISTRIBUTION PROFILING OF AN ELEMENT IN A FILM

RELATED APPLICATION

This is a Divisional application of Ser. No. 11/218,114 filed Aug. 31, 2005 now U.S. Pat. No. 7,411,188, which is related to and claims the benefit of and priority to U.S. Provisional Patent Application Ser. No. 60/698,367 filed Jul. 11, 2005, which is hereby incorporated by reference in its entirety.

FIELD

Embodiments of the present invention pertain to a method and system for extracting depth distribution information of an element or elements deposited in a thin film or an ultra-thin film.

BACKGROUND

Analysis of the composition of a sample is necessary in the manufacture of many different types of devices. The composition of a sample is the concentration of an element and/or chemical species in a thin film. An example of a sample that may require composition analysis is a gate oxide film formed in a semiconductor integrated circuit device. As the density of an integrated circuit chip in a semiconductor device increases and the dimensions of the device continue to be reduced, sample analysis becomes harder and more complex.

For example, recent developments in the fabrication of semiconductor devices may employ shallow implant and/or other ultra-thin structures. In one particular example, gate oxide layers are becoming very thin films, typically less than about 10 nanometers in thickness. Such thin films are difficult to characterize. Such structures will require characterization techniques that have improved sensitivity over conventional characterization techniques. Further, such techniques may also require the characterization to be performed with ample speed.

Various techniques have been used for surface analysis of trace and/or major components in such materials. For example, several of such methods include secondary ion mass spectrometry (SIMS), x-ray photoelectron spectrometry (XPS) (also known as electron spectroscopy for chemical analysis (ESCA)), and Auger electron spectrometry (AES). Such techniques are sensitive to the near-surface region of a material. However, these techniques do not permit measurement of material properties as a function of depth beneath the surface through depth profiling.

In a typical depth profiling process, for example, continuous or periodic ion beam sputtering removes material from the surface of a sample to expose progressively deeper material at one or more various depths of the sample for further measurement and/or analysis. Generally known sputter rates may be used to determine the depth at which the surface measurements are completed. As such, a characterization of the sample as a function of depth beneath the surface can be attained using SIMS, XPS, or AES.

Many of the techniques described above for characterizing thin films are invasive techniques, e.g., they involve destruction of at least one or more portions of the sample. Such techniques, e.g., those that use removal of material during depth profiling, are sufficient in many circumstances, e.g., research and development, product testing, etc., but do not provide for the ability to quickly analyze a thin film such as is necessary in production processes. For example, in such production processes, a thin film being formed typically needs to be analyzed so that such information can be used for production control, product test, etc., without loss of product due to invasive characterization of such films.

SUMMARY

Embodiments of the present invention relate to a method and a system for examining microelectronic structures and specifically to a system and a non-destructive method for detecting the depth distribution of one or more elements in a film using photoelectron spectroscopy.

Embodiments of the present invention also relate to a method and a system for examining microelectronic structures and specifically to a system and a non-destructive method for detecting the centroid of the distribution of one or more elements in a film using photoelectron spectroscopy.

Embodiments of the present invention also relate to a method to design and/or monitor an engineering and/or fabrication process of one of more elements in a film. Accurate materials manufacturing control can be done only when one or more reliable control parameters are available. The determined centroid of the depth distribution (the depth of the center of mass distribution of the element under consideration in a film/layer) and the ratio between the centroid and the thickness of a layer, can be used as control parameters in a process design, monitor and control. Such parameters are accurate predictors of the electrical properties of the engineered/fabricated device on the particular film. For example, for SiON films, in transistor design the determined centroid of the element depth distribution and the ratio between the centroid and thickness of the films correlate to drive current, charge mobility and threshold voltage. The determined centroid can also be used to compute a correction to the dose of an element in a film that can be applied to the standard dose measured by traditional photoelectron spectroscopy (e.g., XPS measurement) thus, improving the correlation between dose and electrical parameters. The dose of a given element can be used to predict EOT (Equivalent Oxide Thickness), leakage current, therefore can also be used in process control. The accuracy of XPS measurement of the dose can be significantly improved using the centroid information.

In a photoelectron spectroscopy measurement system, electrons are ionized from a characteristic element by some means of excitation (for example by illuminating a sample with a photon flux of energy higher than the ionization energy for a given element orbital). The number of ionized electrons that leave the surface of the sample within a certain solid angle are counted in a detector as a function of their energy Electrons ionized from a given element orbital (electron species) will be detected over a broad energy range because they will lose energy through inelastic scattering interaction with the ionized atoms from where they are emitted (intrinsic losses), with atoms in the lattice of the films (bulk scattering) and with the atoms at the interface (surface scattering).

Models of electron transports that account for bulk and surface scattering have been developed and published by several authors, and so are techniques to simulate the energy spectrum of photoelectrons emitted by a given species once their initial energy distribution (intrinsic spectrum) is known.

A photoelectron energy spectrum contains the superposition of spectra of several electronic species emitted by different element with different depth distributions. The amount of energy lost by each species depends on how long the photoelectrons travels within the film—i.e. depends on the depth of origin of the photoelectrons. In theory, given the depth distribution of a single element in a film, the intrinsic spectrum (the energy distribution of photoelectrons leaving the atom) can be derived from the energy spectra of the photoelectrons emitted by each single species of such element, by subtracting the bulk and surface inelastic scattering contribution from the measured energy spectra. In practice, a measured spectrum contains the superposition of several elements and their several species and no mathematical method is available to readily extract the intrinsic spectrum of multiple species when they are superimposed in the spectrum.

In one general aspect of the present invention, several methods to analyze spectra and separate the spectral contribution of one or more species (preprocessed spectrum) are provided.

An embodiment of the present invention pertain to a method to isolate the signal emitted by a first species (signal spectrum) from the signals emitted by different species (background spectra) whose initial emission kinetic energy is larger than the kinetic energy of the first species. The photoelectrons emitted by the different species will lose energy through inelastic scattering and will be detected in the same energy range as the photoelectrons from the first species. So the detected spectrum is the sum of the background spectrum and the signal spectrum.

An embodiment of the present invention pertains to subtracting a background spectrum from a measured spectrum by obtaining an independent measurement of the background spectrum, e.g., by collecting a photoelectron spectrum on a sample (background sample) with the same bulk/surface property of the sample of interest that does not contain the element to be analyzed.

In many instances, such a background sample is not readily available. An embodiment of the present invention pertains to a method of collecting and storing several background spectra on films that are different because of one or more defining parameters (thickness, density . . . ). The background spectra are used to reconstruct an appropriate background for a particular sample by interpolating between these spectra in the parameter space that describe the difference between each of the background samples (difference in thickness, density . . . ).

Another embodiment of the present invention pertains to a method to reconstruct an appropriate background spectrum from prime principles using an electron transport theory. Most of the background elements of which the bulk film is composed are of known or uniform depth distribution. Therefore, when an intrinsic spectrum for each of the species at high emission kinetic energy is known, the full background spectra can be reconstructed, normalized and subtracted to isolate the spectra of the photoelectrons emitted by the species with unknown depth distribution.

An embodiment of the present invention pertain to a method for obtaining intrinsic spectra for multiple species using a set of reference wafers of known depth distribution. The method comprises exciting and acquiring a photo-electron energy signal from a film whose elemental depth distribution is known, and obtaining an intensity spectrum. The intensity spectrum is subdivided in kinetic energy regions (subregions), each one containing the emission energy peak/peaks of one or more species of the same element (same depth distribution) and each one extending to at least the first 20-40 eV below the emission energy. The intrinsic spectrum of each species is determined for each of the energy subregion. The intrinsic spectral determination begins with the subregion at the highest kinetic energy (initial region). The initial region contains radiation emitted by the species whose ionization energy is smaller. The energy spectrum of this species does not require subtraction of a background prior to its analysis (except for stray radiation that can be approximated as a fixed/linear offset). Thus, the intrinsic function for this species in the energy subrange can be extracted using any available deconvolution technique (Fourier transform based inversion, regression methods . . . ). The intrinsic function is then extrapolated to the full energy region for this species. The extrapolation can be done choosing any arbitrary functional form, for instance a simple polynomial fit or an exponential, as long as it satisfy the physics requirements of falling to zero within a reasonable range and generating a background spectra for the analysis of the other species in the film that is consistent with the observation. The intrinsic function of the highest kinetic energy species is then used to regenerate a simulated spectrum in the full energy range. The regenerated spectrum is the background spectrum to the second highest emission kinetic energy species, and therefore will be subtracted from the measured spectrum to obtain a processed spectrum. In this processed spectrum, the species that is emitted in the second highest kinetic energy range can be analyzed in the exact same way as done for the first species.

Embodiments of the present invention also pertain a method of determining a distribution profile for an element in a film. The method comprises exciting and acquiring a photoelectron energy signal from a first film, obtaining a first intensity spectrum associated with the electron energy, and removing a background spectrum from the first spectrum. The background spectrum can be obtained with any of the methods previously as well as herein described. Removing the background spectrum generates a processed spectrum. The method further includes choosing a parameterization for the depth distribution that captures only the available information. The meaning of available information can be explained as followed. A depth distribution can be uniquely identified by its distribution moments (centroid=$1^{st}$ moment, width=$2^{nd}$ moment, asymmetry=$3^{rd}$ moment and so on). The inelastically scattered signal can be expressed as the sum of terms of decreasing amplitude as a function of the ratio between depth and inelastic mean free path each multiplied by the distribution moments. Detection of a given order of the distribution moments with a desired repeatability performance depends on the S/N ratio. The higher the order of the moments to be detected the better signal-to-noise (S/N) will be required. For example, for a given element in a first film the S/N level might be such that only the first moment (centroid) can be detected with the desired repeatability while for an element in a second film the S/N is such that multiple orders of the depth distribution can be detected. In one embodiment, a parameterization of the depth distribution is selected for the first film with a fixed shape distribution and with a variable centroid. The difference in the signal between the real depth distribution and the simplified one will be buried in the noise therefore will not contribute to the signal. In an embodiment of this invention, a parameterization of the depth distribution will consist of a set of appropriately chosen parameterization. In one embodiment, a uniform distribution (homogeneous film) is identified with the width of a step function, and a peak like distribution is identified by the depth of its maximum and the width of the curve. In one embodiment, a Gaussian-shaped distribution is used to detect the first two moments, width and centroid. Once the parameterization of the depth distribution is chosen, the difference between the processed spectrum and a simulated spectrum as a function of the parameters is minimized to find the depth distribution. In one embodiment, a simulated spectrum is obtained using electron transport models and an assumed depth distribution. A conventional minimization algorithm is then used to perform the minimization, such as a Simplex algorithm, a Levenberg Marquardt algorithm or a search for a best match in a database of pre-computed energy spectra. The result of the minimization yields the information about the distribution profile for the element in the film.

Embodiments of the present invention also pertain a method of determining a distribution profile for an element in a film. The method comprises exciting and acquiring a photo-electron energy signal from a first film, obtaining a first intensity spectrum associated with the electron energy, and removing a background spectrum from the first spectrum. The background spectrum can be obtained with any of the methods previously as well as herein described. Removing the background spectrum generates a processed spectrum. The method further includes parameterizing the depth distribution of the element under consideration and minimizing the difference between an independently measured intrinsic spectrum for that species and the intrinsic spectrum derived from the processed spectrum as a function of depth distributions parameters. A conventional minimization algorithm can be used to perform the minimization such as a Simplex algorithm, a Levenberg Marquardt algorithm or a search for a best match in a database of pre-computed energy spectra. The result of the minimization yields the distribution profile for the element in the first film.

In one embodiment, from the distribution profile, a centroid for the element is determined. The centroid of an element in a film is the depth of the center of mass of the concentration of the element in the film. Most of the physical properties of the film can be determined by the knowledge of the centroid. In one aspect of the present invention, the centroid value is used to predict the electrical properties of a device fabricated on or in the film and/or control or monitor the fabrication process of the device.

Embodiments of the present invention also provide a method to simulate, in real time, a modeled spectrum with a known distribution profile. Statistical coefficients (known in electron transport theory as the Partial Intensities-PI coefficients) characteristic of the depth distribution of a given species and the scattering process (elastic and inelastic) can be pre-computed, for example, using a Monte Carlo or other suitable methods. The PI coefficients are pre-computed for a sparse set of depth distributions and stored in a PI coefficients database. Such set of PI coefficients can be organized in the database as a function of parameters defining the associated depth distributions. Several interpolation techniques can be used to interpolate the PI, e.g. N-dimensional linear or higher order polynomial interpolation. During a real time simulation of the spectrum associated to an arbitrary depth distribution the appropriate PI coefficients are found by interpolating the pre-computed PI coefficients in the space of parameters describing the depth distribution. The interpolated PI coefficients are then used to reconstruct the spectrum which is used as a simulated spectrum (for example a background spectrum or a signal spectrum pertaining to the element of interest) or is used to reconstruct the scattering contribution that can be subtracted from a processed spectrum (as previously discussed) to obtain an intrinsic spectrum. The same type of interpolation scheme can be done if the full spectra associated to the sparse set of depth distribution is stored, but that would require a much larger storage memory for the database.

In another aspect of the present invention, a method to extract the centroid of an element depth distribution directly from the attenuation of multiple species of the same element is described.

In another aspect of the present invention, a method of determining a centroid of a distribution profile for an element in a sample film is provided. The method comprises exciting and acquiring a photo-electron energy signals from two species of the same element in the film and obtaining an intensity ratio for the photoelectrons signals (e.g., for nitrogen in SiON, an N1s photoelectron and an NKLL Auger photoelectron are acquired). A set of ratios of signal intensities is obtained for a set of samples of known centroids of a particular element (e.g., nitrogen) to generate a calibration function. The measured ratio of signal intensities of the sample film is correlated to the calibration function to determine the centroid of the distribution profile for the element. The centroid of the element in the film is the depth of the center of mass of the concentration of the element in the film. Most of the physical properties of the film can be determined by using the centroid value. In one aspect of the present invention, the centroid value is used to predict the electrical properties of a device fabricated in or on the film and/or control/monitor the fabrication process of the device.

Depth distribution information can also be extracted from the attenuation of the intensity of the unscattered electrons collected at different emission angles, for instance using ARXPS. The method described in literature is based on the assumption that unscattered electrons emitted at depth z and collected at emission angle $\theta$ have been attenuated by a factor $$e^{\frac{z}{\lambda \cos \theta}}.$$

A coarse depth distribution can be found by optimizing the difference between the attenuation measured as a function of theta and the attenuation expected assuming a depth distribution for the element under consideration, i.e. minimizing $$MeasuredAttenuation(\theta) - \int dz N(z) e^{\frac{z}{\lambda \cos \theta}}$$

as a function of the element depth distribution $N(z)$. Such measurement is impacted by systematic errors arising from neglecting the angular dependence of the attenuation that all electrons suffers crossing the material/vacuum interface and the systematic error introduce by neglecting the angular straggling due to elastic scattering.

In one embodiment of this invention we claim a method to collect electron spectra at various collection angles, preprocess the data by eliminating surface scattering contribution from the spectra using a deconvolution technique (one or more techniques can be used for example fast Fourier transform deconvolution or Dr. Werner deconvolution theorem) to subtract the systematic error due to interface crossing prior to minimization. For samples engineered in such a way that the depth distribution of the element under consideration extend to the typical elastic scattering length the preprocessed signals can be analyzed including the effect of elastic scattering to improve the accuracy of the result. That is done by including elastic scattering effects in modeling the attenuation. The difference between the measured attenuation as a function of angle and the attenuation predicted for a given depth distribution by a Monte Carlo simulation that includes elastic scattering effects is minimized as a function of assumed depth distribution. The impact on minimization speed of the Monte Carlo simulation can be mitigated by parameterizing the depth distribution as previously described, pre-computing the attenuation as a function of angles for a sparse set of parameters and store it in the database. The attenuation values needed for a specific depth distribution can be obtained by database interpolation.

In several embodiments of the present invention, we have described embodiments of deriving signals by interpolations from a set of pre-measured or pre-computed spectra as a technique to obtain an expected signal without specifically measuring the expected signal or generating it. A signal generated during minimization process is solely used to compute a figure of merit. A figure of merit is usually defined as a single number that quantify the difference between the measured and simulated signal, for instance an Mean Square Error is defined as $$\text{Figure Of Merit} = \sum_{Energy} (\text{Measured(Energy)} - \text{Simulation(Energy)})^2$$

An alternative way to solve a minimization problem is to first pre-compute the figure of merit associated with all pre-computed simulated spectra contained in a sparse database (Sparse Figure of Merit). Each pre-computed value of the sparse figure of merit is associated with a set of parameters uniquely defining a depth distribution. The sparse figure of merit can be finely interpolated to produce a figure of merit surface. The minimum of that surface in the depth distribution parameter space can easily be found by one of the many minimum search methods, i.e., root finding methods or steepest descent methods. The minimum of that surface defines the depth distribution profile for the element of interest.

Other embodiments are also described. Other features and advantages of the present invention will become apparent from the following detailed description, taken in conjunction with the accompanying drawings, which illustrate, by way of example, the principles of the invention.

BRIEF DESCRIPTION OF THE DRAWINGS

The embodiments of the present invention are illustrated by way of example and not by way of limitation in the figures of the accompanying drawings in which like references indicate similar elements. The invention may best be understood by referring to the following description and accompanying drawings that are used to illustrate embodiments of the invention. It should be noted that references to "an" or "one" embodiment of the invention in this disclosure are not necessarily to the same embodiment, and they mean at least one. In the drawings:

FIGS. 15-16 illustrate exemplary methods of simulating one or more spectrum using the simulated spectrums for background subtraction and methods of analyzing multiple elements in a film.

DETAILED DESCRIPTION

Figure 1:
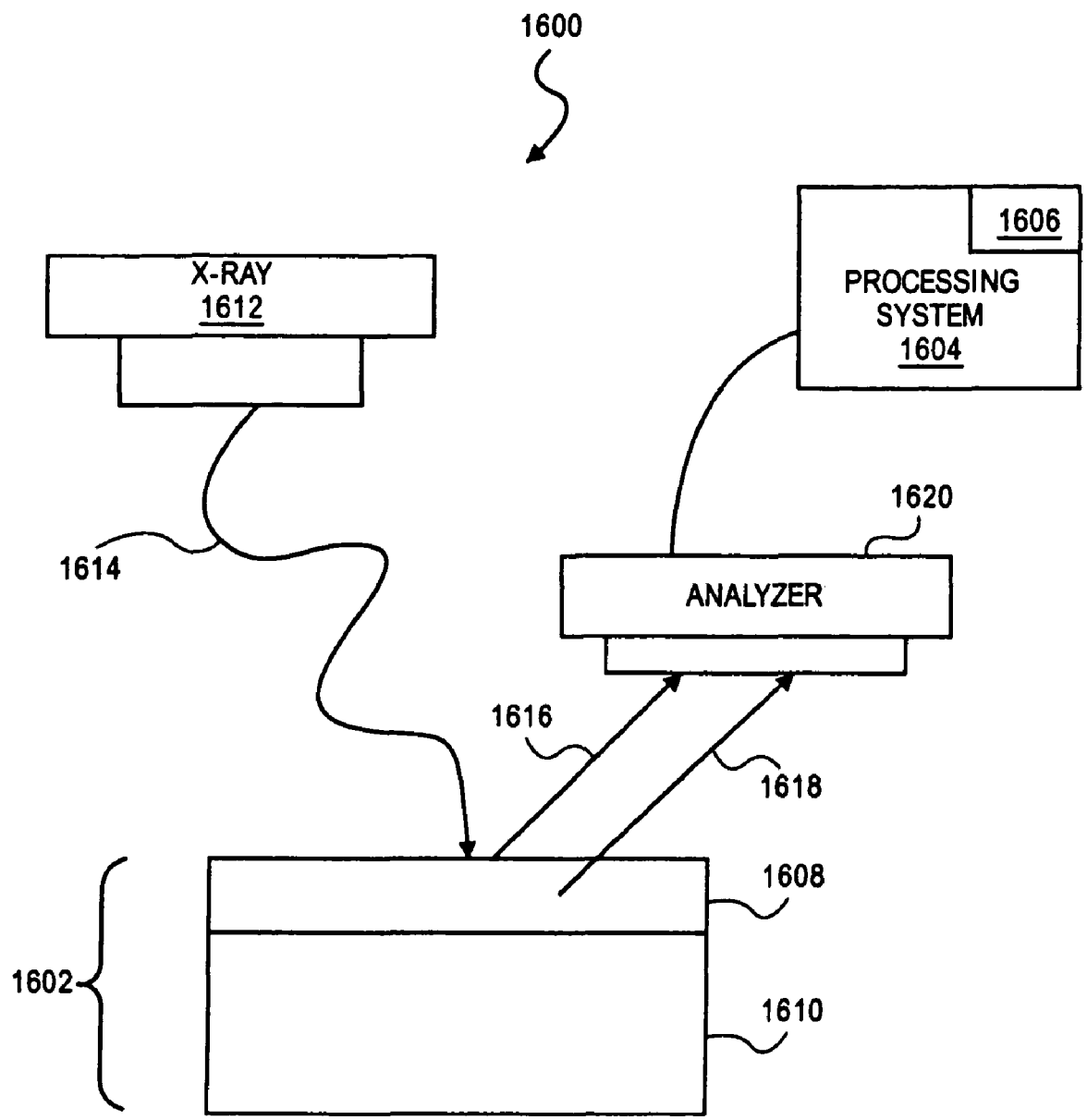
FIGS. 1-3 illustrate exemplary analysis systems that can be used for certain embodiments of the present invention.

Exemplary embodiments are described with reference to specific configurations and techniques. Those of ordinary skill in the art will appreciate the various changes and modifications to be made while remaining within the scope of the appended claims. Additionally, well known elements, devices, components, circuits, process steps and the like are not set forth in detail.

Embodiments of the present invention pertain to a method and system for extracting depth distribution information and/or a centroid value of an element or elements deposited in a thin film or an ultra-thin film. Such a film would have a film thickness below 20 nm or most often, below 10 nm, and even below 2 nm. It is anticipated that the embodiments of the present invention are similarly applicable to analysis of films with thickness about 20 nm or greater. In one general aspect of the present invention, a depth distribution profile for an element in a film is determined. First, one or more measured energy spectra (or a measured energy signal) collected at one or more angles relative to the normal direction to the sample surface are collected. Second the background of the measured energy spectra that is obtained for the element in the film is subtracted from the measured energy spectrum. The background information to be used is obtained by an interpolation method using a selected set of background spectra. In one embodiment, the measured energy spectrum is obtained using a photoelectron spectroscopy system such as x-ray photoelectron spectrometry (XPS). The measured energy spectrum with the background removed is referred to as a processed energy spectrum for the element. Next, the processed energy spectrum is matched against a modeled or simulated energy spectrum or energy signal. In one embodiment, an optimization and minimization method is performed to match the processed spectrum to a simulated spectrum as a function of selected parameters that define the distribution profile for the element. When the difference between the processed spectrum and a particular simulated spectrum is the smallest, the parameters associated with the particular simulated spectrum provide the distribution profile for the element in the film.

In another general aspect of the present invention, a centroid value for the elemental depth distribution is determined by utilizing a ratio of signal intensities that originate from emission signals of different kinetic energies but of the same element (e.g., for nitrogen in SiON, an N1s photoelectron and an NKLL Auger photoelectron). Different emission lines due to the same element (different species) will have different kinetic energies. Having different kinetic energies, the electrons from each of the species will experience different attenuation when they traverse a film layer. The higher energy electrons will experience less attenuation when passing through material than lower energy electrons. For instance, taking nitrogen as an exemplary element, the electron from the N1s species of nitrogen has a higher electron energy than the electron form the NKLL species. The centroid of the nitrogen distribution in the SiON film, can be determined using the ratio of N1s/NKLL intensities. The intensity ratio is governed by the different attenuation length $\lambda(N1s)$ and λ(NKLL) at the different emission energy for the N1s and NKLL species, respectively. Given that the signals originate from the same element and the same in-depth distribution, the signal ratio correlates with the centroid of the element in the film. A set of ratios of signal intensities is provided for a set of known centroid for a particular element (e.g., nitrogen) to generate a calibration function. The measured ratio of signal intensities of the sample film is correlated to the calibration function to determine the centroid of the distribution profile for the element.

Throughout this discussion, the term "element" may be used to refer to a chemical composition of a specific layer or substrate. The term "element" may also be used to refer to an elemental species deposited in a specific layer or substrate. For example, a hafnium oxide layer includes an element of hafnium and oxygen or a silicon oxynitride layer includes an element of silicon, nitrogen, and oxygen. An "electron species" or a "photoelectron species" refer to an electron having a characteristic energy. A single element may emit several different electron species. For example, a silicon substrate may emit two different characteristic electrons having different kinetic energies. One electron may be emitted from the 2p orbital of the silicon atom, while the other electron may be emitted from the 2s shell of the silicon atom. In another example, a silicon oxynitride layer may emit two different characteristic electrons for the nitrogen element having different kinetic energies. One electron may be emitted from the N1s orbital of the nitrogen atom, while the other electron may be emitted from the NKLL (Auger region) of the nitrogen atom. An electron signal hereinafter refers to a stream of electrons belonging to a specific electron species. For example, a "nitrogen N1s electron signal" comprises electrons emitted by the nitrogen atom from the N1s region. For example, a "nitrogen NKLL electron signal" comprises electrons emitted by the nitrogen atom from the Auger region or NKLL region. Many of the embodiments discussed below refer to photoelectrons or electrons that are emitted when a layer is bombarded with photons. Each elemental species may emit one or more photoelectron species, which may comprise a photoelectron signal. An electron energy signal may have a single value or may be indicated in a spectral line.

As used herein, characterization or analysis refers to the determination of one or more characteristics of the sample being analyzed. For example, characterization may refer to a distribution profiling or depth profiling of a sample or portion thereof, a determination of concentration of components in a sample, a distribution of such components, or a determination of one or more other physical or chemical characteristics of the sample, e.g., thickness of regions, bonding states in the regions, elemental and chemical composition in the regions. The present invention is particularly beneficial in the determination of the concentration or dose of components (e.g., elements and/or chemical species) versus depth in a sample film.

Throughout the discussion, the term "distribution profile" may be used generally to refer to deposition depth, deposition profile, deposition width, and centroid value of an element deposited in a film. A "centroid value" or a "centroid" of a distribution is defined as $$\text{centroid} = \frac{\int_0^\infty N(z) z \, dz}{\int_0^\infty N(z) \, dz}$$

where N(z) is the concentration depth distribution and z is the depth. The centroid is thus the average depth of an element in a film, e.g., the nitrogen in an SiON film, or the depth of the center of mass of the element. A "dopant" generally refers to an element (e.g., nitrogen) being deposited in a film. A "dose" generally refers to a count or concentration of an element or a dopant being deposited in a film.

Figure 2:
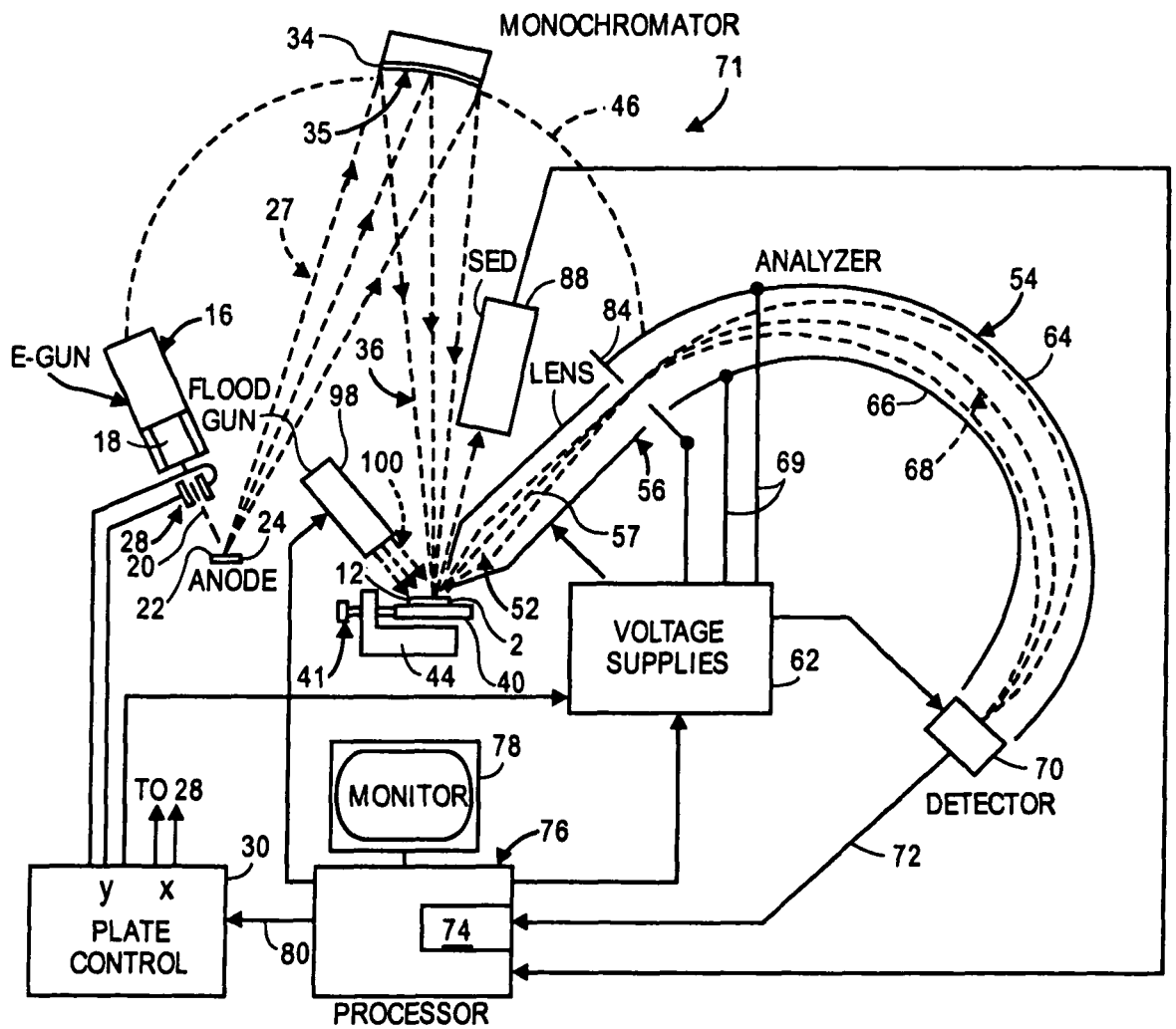
Figure 3:
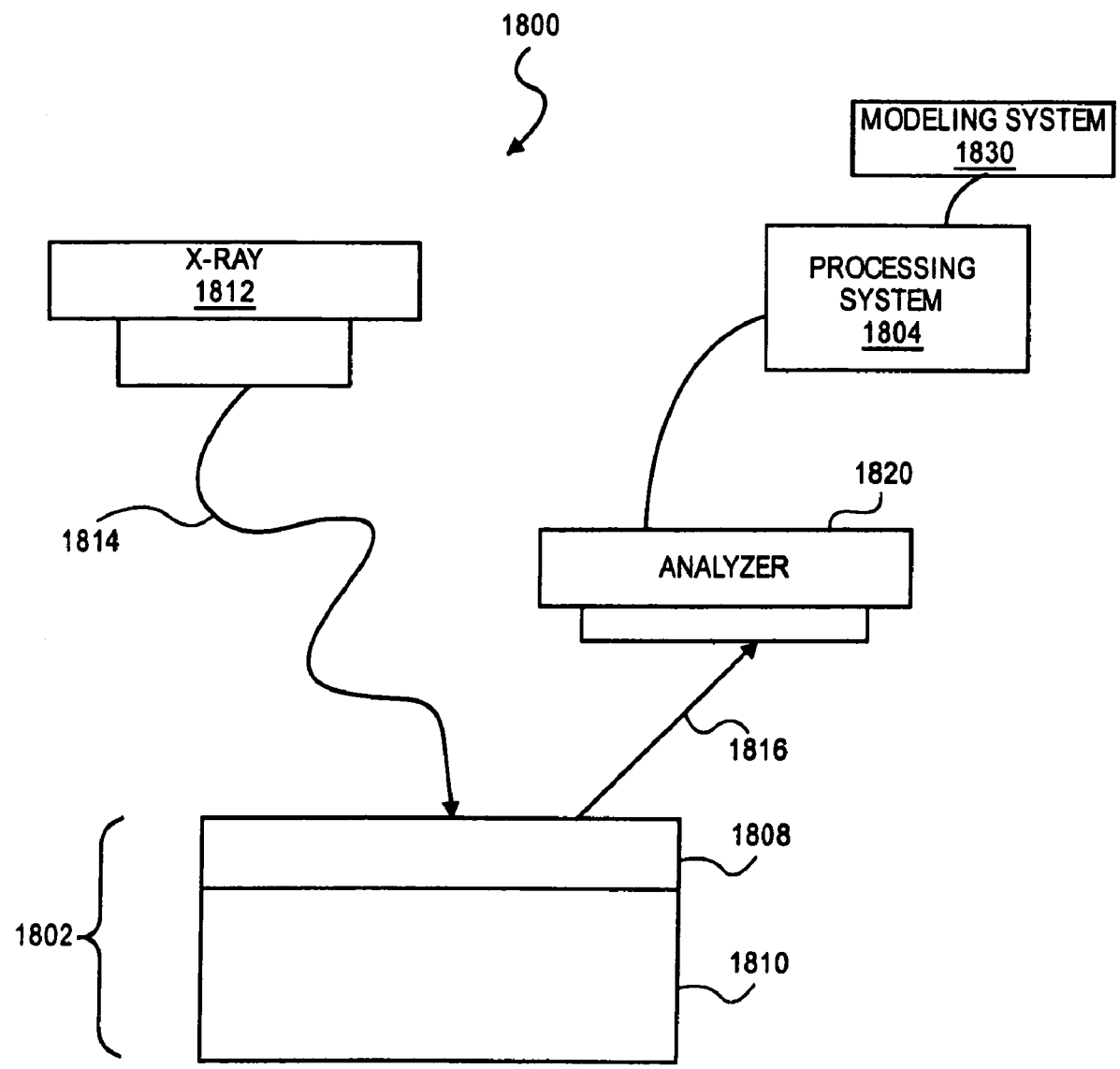

FIGS. 1-3 illustrate exemplary analysis systems that can be used with one or more embodiments of the present invention. FIG. 1 generally shows one embodiment of an illustrative analysis system 1600 operable for use in characterizing a sample 1602. The analysis system 1600 includes a processing system 1604 (e.g., a computer apparatus) operable under control of one or more programs 1606 to carry out one or more various depth profiling, centroid determination, and/or characterization processes in according to embodiments of the present invention.

The sample 1602 having a sample surface 1608 may be formed of any one or more components and/or which may be formed on a substrate 1610. The term component is defined herein as one or more elements and/or chemical species. For example, such components may include elements and/or chemical species composing materials used in semiconductor fabrication, magnetic storage media, or any of the other various applications described above. In other words, for example, in the context of semiconductor fabrication the sample may include layers formed of oxygen, silicon, carbon, fluorine, silicon dioxide, nitrogen, etc.

The processing system 1604 includes a computing system operable to execute the computer program or software 1606 to provide for the characterization of samples according to certain embodiments of the present invention. Although the processing system 1604 may be implemented using the program 1606, executable using a processor apparatus, other specialized hardware may also be used to provide certain functionality required to provide a user with characterization of a sample. As such, the term processing system 1604 as described herein includes any specialized hardware or computer in addition to processor apparatus capable of executing various software routines.

The processing system 1604 may be, for example, any fixed or mobile computer system, e.g., a personal computer, and/or any other specialized computing unit provided as a functional part of or as a supplement to an analysis instrument used according to the present invention. The exact configuration of the computer system is not limiting and most any device capable of providing suitable computing capabilities and/or control capabilities may be used according to the present invention. Further, various peripheral devices, such as a computer display, a mouse, a keyboard, a printer, etc., are contemplated to be used in combination with a processor in the processing system 1604. For example, a computer display printer may be used to display depth profile information, e.g., depth profile curves showing concentration of components (e.g., elements and/or chemical species) at depths of the sample, distributions of components across a sample at a particular depth, spectra of the components, etc.

The analysis system 1600 according to the present invention includes an x-ray source 1612 operable to irradiate the sample 1602 with x-rays 1614 resulting in the escape of photoelectrons therefrom. As shown in FIG. 1, the x-rays 1614 penetrate deep into the sample surface 1602, exciting photoelectrons 1616 and 1618 to escape from the sample 1602.

The analysis system 1600 also includes an analyzer 1620 operable to detect photoelectrons 1616 and 1618 escaping from the sample. The analyzer 1620 is used to detect photoelectrons for generation of a signal representative thereof to be used in the distribution profile analysis for the sample 1602. Signals from the analyzer corresponding to intensity of detected photoelectrons are provided to the computer apparatus, which operates on the signals to provide photoelectron energy information, and thereby information on components that are present in the sample surface at the depth being analyzed. The analyzer system 1600 can be replaced by or combined to a conventional XPS system, an Ultraviolet Photoelectron Spectroscopy (UPS) system, an Auger Spectroscopy system, etc.

FIG. 2 shows in more detail one illustrative embodiment of portions of an analysis system 71 operable for carrying out the characterization according to certain embodiments of the present invention. The analysis instrument 71 shown in FIG. 2 for analysis of a sample 2 (which can be the sample 1602 previously shown or other samples) provides a more detailed illustrative embodiment of the x-ray source 9, the analyzer 7, and the computer apparatus 13 shown generally in FIG. 1. FIG. 2 has previously been described in U.S. Pat. No. 5,315,113 to Larson et al., issued 24 May 1994, and entitled "Scanning and High Resolution X-ray Photoelectron Spectroscopy and Imaging." The detailed diagram of FIG. 2 is but one illustrative embodiment of an x-ray source and an analyzer that may be used according to the present invention and is not to be construed as limiting the present invention to any particular components shown therein.

The instrument 71 of FIG. 2 includes an electron gun 16 having an appropriate electron lens system 18 for focusing the electron beam 20 onto the surface 22 of a target anode 24. The electron gun 16 may be a conventional type, modified to optimize for higher power and larger beam size. The gun beam 20 is focused to a selected spot on the anode surface 22. The spot is preferably as small as practical, e.g., down to about 4 microns. The focusing of the beam 20 onto the spot of the anode surface results in the generation of x-rays 27 from the anode 24 and, in particular, from the selected anode spot. The electron gun may be any suitable gun such as one operable at 20 kV over 1 watt to 60 watts with a selectable beam size of 4 microns to 50 microns, as described in U.S. Pat. No. 5,315,113.

The target anode 24 may be formed of any metal such as aluminum that provides a desired x-ray emission energy band. For example, the band is generally substantially a line of small energy width. Preferably, the target anode is at or near ground potential, and the gun cathode is operated at a negative voltage, for example, −20 kV, with respect to the anode to effect generation of x-rays including the desired band of x-rays of predetermined energy. In one preferred embodiment, the selected energy band is the aluminum K-alpha line at 1.4866 keV.

Deflection plates 28 selectively direct or aim the electron beam 20 from the electron gun 16 to the spot on the anode 24 which is selected out of an array of such spots on the anode surface 22. Voltages from a deflection plate control 30, controlled by a processor 76 via line 80, are applied to the deflector plates, which are arranged in both x and y axes, to establish the amount of deflection of the beam, and thereby the selected position of the spot. The spot may be held stationary. Alternatively, the control 30 may provide rastering of the focused electron beam 20 across the flat surface of the anode, e.g., over the array of anode spots across the anode surface, and the x-rays 27 are emitted sequentially from successive anode spots. For example, raster speed may be 100 Hz in the dispersive direction and 10 kHz in the non-dispersive direction.

A Bragg crystal monochromator 34, advantageously single-crystal quartz, is disposed to receive a portion of the x-rays 27 from the anode 24. The monochromator has a crystallographic orientation and a concave configuration 35 to select and focus a beam of x-rays 36 in the desired energy band, e.g., the K-alpha line, as an x-ray spot on the sample surface 12 to be analyzed. The x-ray spot is an image of the anode spot on the sample surface 12. Alternatively, rastering of the x-ray spot may be used to cover a desired area of the sample surface. The sample 2 rests on a stage 40 advantageously having orthogonal micrometer positioners 41 for manual or motorized positioning with respect to a support 44 in the instrument. The sample 2 may be moved to provide coverage over an even larger surface area.

Although a Bragg crystal monochromator is preferred, other focusing apparatus may be suitable. Such focusing apparatus may include grazing incidence mirrors, Fresnel zone plates, and synthetic multilayer devices of alternating high and low density material (e.g., tungsten and carbon). In each case, the reflector is curved to focus the diffracted x-rays onto the specimen.

A suitable arrangement of components for the analysis instrument 71 is based on the conventional Rowland circle 46. In this arrangement, the anode surface 22, the crystal 34, and the sample surface 12 are substantially on the circle, for example, as taught in U.S. Pat. No. 3,772,522, to Hammond et al., issued 13 Nov. 1973 and entitled "Crystal Monochromator and Method of Fabricating a Diffraction Crystal Employed Therein."

The x-rays 36 cause photoelectrons 52 to be emitted from the selected active pixel area of the sample. The electron energies generally include a low energy peak in the range of up to 10 eV, usually about 2 to 5 eV, plus higher kinetic energy peaks or lines characteristic of chemical species (e.g., chemical elements and/or their electron bondings) in the selected pixel area. In the case of rastering, the characteristic photoelectrons vary with any varying chemistry across the array of pixel areas, and the low energy electrons (commonly known as "secondary electrons") vary with topography, as well. Detection and/or analysis of the photoelectrons are used to provide information regarding the sample surface at a selected pixel area or across the rastered array of areas of the sample surface. There also may be Auger electrons, which, for the present purpose, are included in the term "photoelectrons" as they are caused by the x-rays.

In one embodiment of the invention, an electron energy analyzer 54 receives a portion of the photoelectrons 52. The analyzer may be a known or desired type, generally either magnetic or electrostatic, which deflects the photoelectrons in a predetermined path 68 according to electron energy and then to a detector 70. A selected control, generally an electrical signal (current or voltage), is applied to the deflector to establish the amount of deflection and so is representative of selected energy of photoelectrons deflected in the predetermined path. In a magnetic analyzer such as a magnetic prism, a current signal through the magnet coils is appropriately selected, and in an electrostatic analyzer a deflecting voltage signal is selected.

Figure 4:
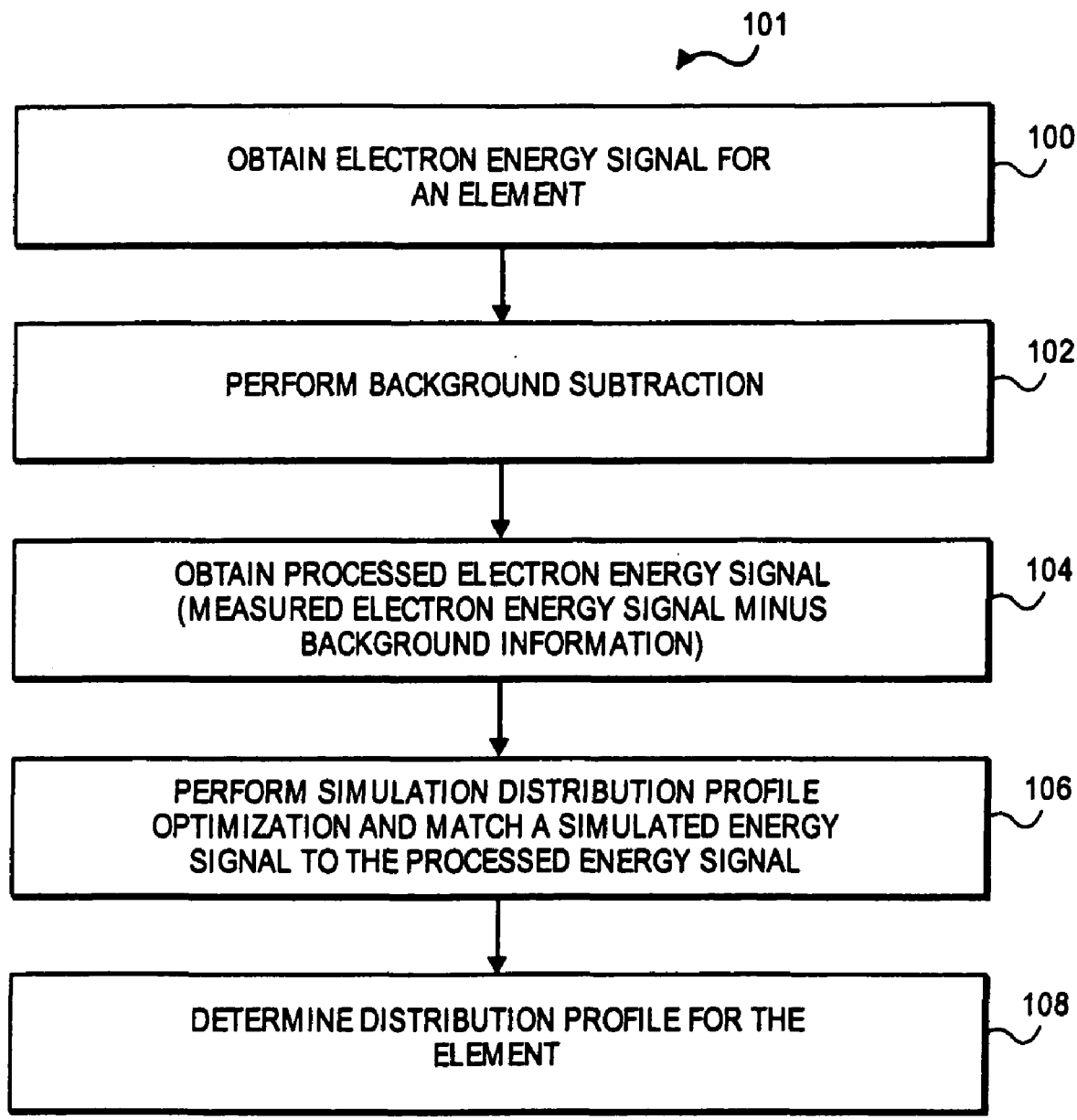
FIG. 4 illustrates an exemplary process of analyzing an distribution profile of an element in a film.

One useful type of electrostatic energy analyzer is a cylindrical type described in U.S. Pat. No. 4,048,498, to Gerlach et al., issued 13 Sep. 1977 and entitled "Scanning Auger Microprobe with Variable Axial Aperture." In a preferable alternative, as shown in FIG. 4, the analyzer 54 is a hemispherical type as described in U.S. Pat. No. 3,766,381, to Watson, issued 16 Oct. 1973 and entitled "Apparatus and Method of Charge-Particle Spectroscopy for Chemical Analysis of a Sample." The analyzer also includes a lens system 56 such as an electrostatic lens for the input to the analyzer. The lens system 56 has a central axis 57 therethrough along which system 56 lies. The lens system 56 may combine objective and retarding functions to collect photoelectrons emitted from the effective pixel area and direct them into the analyzer in the desired kinetic energy range.

The electrostatic lens system 56 may be conventional, for example, a PHI Omnifocus IV™ lens available from Physical Electronics Inc. The lens should include pairs of orthogonal deflection plates with applied voltages from a source 62. The voltages are selected, varied, or oscillated via the processor 76 in cooperative synchronization with positioning or rastering of the primary electron beam 20, under control of the processor, to centralize off-axis photoelectrons so that a substantial portion of the electrons reach the slit 84 and enter into the analyzer 54.

An alternative for the objective lens function is a magnetic lens, advantageously of a type variously known as an immersion lens, a single pole piece lens or a snorkel lens as described in U.S. Pat. No. 4,810,880, to Gerlach, issued 7 Mar. 1989 and entitled "Direct Imaging Monochromatic Electron Microscope." This objective lens is situated below the sample so that the magnetic field of the lens collects a substantial portion of the emitted photoelectrons from the sample surface. To achieve this, the sample is placed proximate the immersion lens, the sample being interposed between the immersion lens and a separate electrostatic lens which form the lens system. More generally, the sample is located between the immersion lens and the analyzer. The magnetic lens may have a collection zone of electrons emitting from a portion of specimen surface being rastered.

Yet further, preferably, the lens system is an electrostatic lens with two spherical grids, similar to the Omega™ lens available from Physical Electronics Inc. Such a lens system is used in the PHI Quantum 2000 Scanning ESCA Microprobe™ available from Physical Electronics Inc.

With a selected voltage from a voltage source 62 applied via lines 69 across the hemispheres 64, 66 of the analyzer, electrons of selected energy travel in a narrow range of trajectories 68 so as to exit the analyzer into the detector 70. The latter may be a conventional multichannel detector, for example, having 16 channels for detecting a small range of electron energies passed by the analyzer in slightly different trajectories. A further lens (not shown) may be placed between the analyzer and the detector, if desired or required for certain types of detectors.

Signals from the detector 70 corresponding to intensity of photoelectron input are carried on a line or lines 72 (via an appropriate amplifier, not shown) to an analyzing portion 74 of the processing unit 76, which combines control electronics and computer processing. The processing provides electron energy information and thereby information on components that are present and emitting the photoelectrons from the particular sample surface area.

The information is stored, displayed on a monitor 78, and/or printed out in the form of images, numbers, and/or graphs. By cooperating the display (which herein includes the processing) with the electron beam directing means 28, 30, via line 80 from the processor to the controller 30, a mapping of the components in the selected or scanned surface area is effected and displayed. The mapping provides sample surface information corresponding to the selected pixel area location, or the rastered array of pixel areas on the sample surface.

Other portions of the instrument 71, such as the secondary electron detector 88 and electron gun 98 providing ions 100, are used as described in U.S. Pat. No. 5,315,113.

According to the present invention, and advantageously used in the characterization of thin films, the lens system 56 is positioned at an analyzer angle of a constant angle for improved and faster data collection. The lens system 56 generally extends along a central axis 57 from a photoelectron receiving end 59 to an end coupled to hemispherical portions of the analyzer 54.

Returning to the analysis system 1600 (FIG. 1), the system is configured to excite more than one electrons from the same sample 1602 at the same depth. For example, the system 1600 is configured to excite two different photoelectrons from the sample 1602. In one embodiment, the sample comprises an SiON film and the electrons to be excited from the SiON film associate with the nitrogen element deposited in the SiON film. FIG. 1 illustrates that the analysis system 1600 is configured to excite two different photoelectrons 1616 and 1618. In one embodiment, the photoelectron 1616 is from the N1s region of the film and the photoelectron 1618 is from the Auger (NKLL) region of the film. The X-ray source 1612 is illustrated as one unit but may include different sources that can cause two or more different photoelectrons to be exited for the sample 1602.

An analysis system such as the system 1600 is particular useful for carrying out one or more exemplary embodiments of the present invention. For instance, the system 1600 is used to take measurements for the samples with known distribution profile that are used to generate a calibration function that is used to analyze an unknown sample. The measurements for the calibration function is stored and processed by the processing system 1604. When the unknown sample is measured, the measurements form the unknown sample is also processed by the processing system 1604 and interpolated using the calibration function in provided via the processing system.

FIG. 3 illustrates another exemplary analysis system 1800 that can be used for certain embodiments of the present invention. The analysis system 1800 is similar to the system 1600. In addition to some of the components similar to the system 1600, the system 1800 includes a modeling system 1830 that can be used to generate signal spectra or signal values associated with simulated distribution profiles. Similar to the system 1600, the system 1800 includes an X-ray source 1812, an analyzer 1820, and a processing system 1804. A sample 1802 that includes a film 1808 formed on a substrate 1810 can be analyzed using the system 1800.

The system 1800 can be used to carry out one or more exemplary embodiments of the present invention. Generally, in these methods, a sample film is analyzed by having a measured spectrum for a particular element (e.g., nitrogen) in a sample film (e.g., SiON) processed and compared to a simulated spectrum to determine the distribution profile of the element in the sample film. In one example, an electron energy signal for nitrogen is obtained by the X-ray source 1812 sending an x-ray into the sample film 1808 and excites the photoelectron 1816. The analyzer 1820 detects the photoelectron 1816 and produces a measured signal intensity associated with the photoelectron 1816

FIG. 4 illustrates an exemplary analysis method 101 that illustrates a general novel approach of determining a depth distribution profile of an element deposited in a thin sample film. The thin sample film may be deposited or otherwise formed on a substrate or other film(s). At operation 100, an electron energy signal for an element is obtained. A signal of the element may be represented as an energy spectrum of the element. The element is deposited in a sample film or in a substrate using various methods. Often, for an element deposited in a film, the depth of the element deposition, the distribution of the element, and/or the distribution profile in the film needs to be analyzed. At box 102, a background subtraction is performed. At box 104, a processed electron energy signal is obtained. When the background is subtracted from the electron energy signal, the signal value obtained is referred to as a "processed electron energy signal." The background that is removed includes the energy signal obtained due to the bulk material in the sample film and without the element of interest. Removing the background provides for the isolation of the energy signal of the element of interest only so that analysis can be performed for the element deposited in the sample film. To begin the distribution profile determination, for the element, at box 106, a simulation distribution profile is varied (optimization) until the simulated energy signal associated with the simulation distribution profile matches the processed electron energy signal. In one embodiment, the processed electron energy signal is matched to a simulated energy signal using a minimization and optimization algorithm such as a Simplex algorithm or Levenberg Marquardt algorithm. When the difference between the processed electron energy signal and a particular simulated energy signal is the smallest, a matched is obtained. The distribution profile of the element under consideration is therefore determined in box 108 as the one simulated distribution profile that was used to compute the best matching simulated spectra to the processed spectrum.

Figure 5:
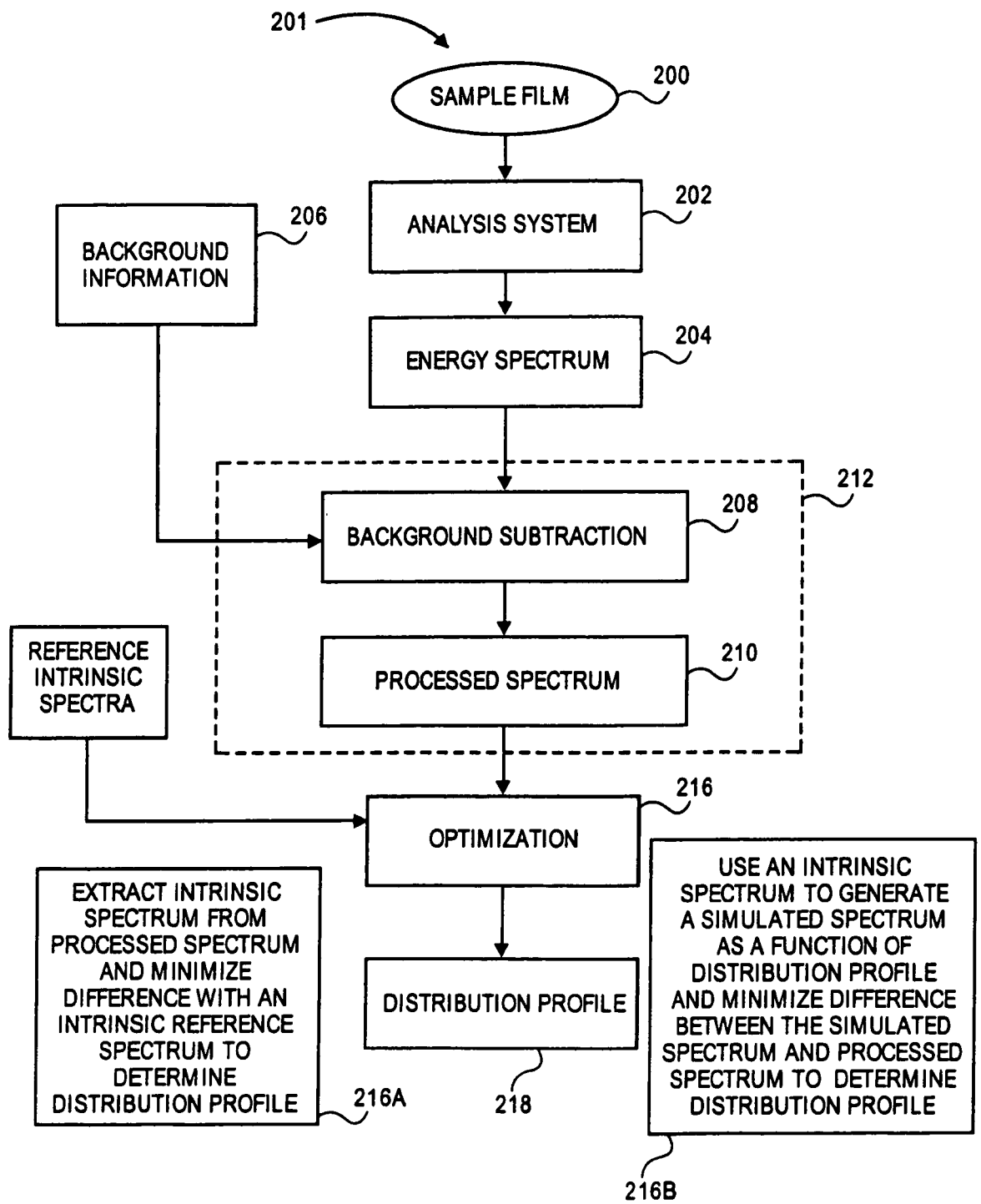
FIG. 5 illustrates an exemplary method of determining a distribution profile of an element in a sample film.

The following discusses in more details the various aspects of the invention according to the exemplary method 101. FIG. 5 illustrates an exemplary embodiment of a process 201 that analyzes distribution profile of an element deposited in a sample film. In one embodiment, a substrate (such as a wafer) that has the sample film with the element of interest to be analyzed is provided (box 200). An element of interest is nitrogen deposited in a SiON film, in one embodiment. In other embodiments, other elements deposited in the same film or other films are provided. Numerous elements deposited in various types of sample films can be analyzed using embodiments of the present invention.

The sample film is placed in an analysis system such as those discussed in reference to FIGS. 1-3. An example of an analysis system includes XPS. Other equipments that can excite electrons from a film and produce a readable result from the energy released from the electron or the energy used to excite the electrons can be used. In one embodiment, the sample film is irradiated with x-rays (using an x-ray source provided in the analysis system) resulting in the escape of photoelectrons therefrom. The escaped photoelectrons are detected by a detector provided in the analysis system. The detected photoelectrons at each energy are counted and translated into energy signal (spectra) representative of the film and reported. The energy signal is used for the analysis of the element. At 204, a measured energy signal or spectrum for the element is obtained.

Next, at 212, the measured energy signal/spectrum is processed. In one embodiment, in processing the measured energy signal/spectrum, the background information 206 of the measured energy signal/spectrum is removed or subtracted as shown at box 208. After the background information is removed, a processed spectrum is obtained at 210.

At 216, the processed spectrum is subjected to optimization to determine the depth distribution profile of an element in the sample film. At 216A, the depth distribution is obtained by minimization of the difference between the processed energy signal/spectrum and a simulated spectrum as previously described, e.g., using a minimization algorithm. An intrinsic spectrum is extracted from the processed spectrum and subjected to a minimization with an intrinsic spectrum with a known distribution profile to determine the distribution profile of the element.

Alternatively, at 216B, the depth distribution is obtained by minimization of the difference between a reference intrinsic spectrum and the intrinsic spectrum derived from the processed energy signal/spectrum as described. The intrinsic spectrum is used to generate a simulated spectrum with a known distribution profile and is minimized against the processed spectrum to determine the distribution profile.

The distribution profile for the element is determined based on the result of the minimization/optimization process at 218.

The background energy signal/spectrum is the signal/spectrum is emitted by elements of the sample film other than the element of interest, at emission kinetic energy higher than the species under analysis. In one embodiment, to find the appropriate background energy signal/spectrum, a set of reference background signals/spectra associating with a set of reference films is obtained. Each reference film is comparable to the sample film in that it is similarly treated and formed except for the lack of the element under consideration. In other words, each reference film is like the sample film except that the reference film does not have the element of interest deposited therein and may have a thickness different or slightly different from the thickness of the sample film. The same analysis system used to analyze the sample film is used to obtain the background energy signal/spectrums for the reference films. Depending on the thickness of the sample film, a particular background energy signal/spectrum is either reconstructed from the set by interpolation or just selected from the set of reference background spectra—if the correct thickness is available.

Figure 6:
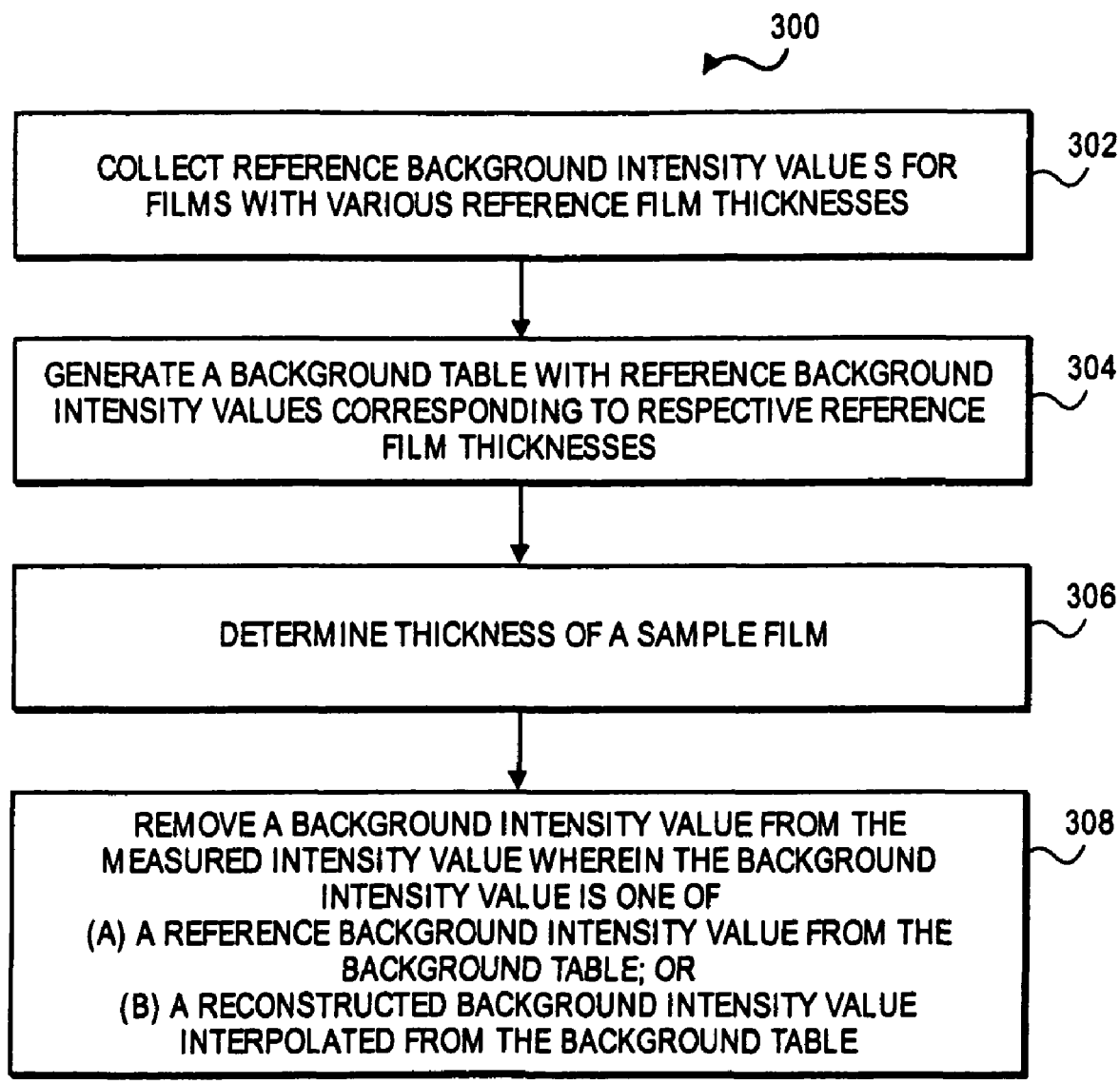
FIG. 6 illustrates another exemplary method of determining a distribution profile of an element in a sample film.

FIG. 6 illustrates an exemplary embodiment method 300 of a background subtraction method for a measured energy signal/spectrum obtained for a sample film in according to the present invention. At 302, a set of reference background intensity spectra for various reference films is collected. The reference films include films having various reference film thicknesses. The reference film thicknesses may range from 1-50 nm, which is only an exemplary range of thickness. The chosen reference film thicknesses may cover a wide selection of thicknesses to a smaller selection of thickness that the sample film or the like is expected to fall within. In one embodiment, the background intensity spectra are the photoelectron energy signals of the reference films taken using the analysis system 202 previously mentioned. The intensity spectra taken for the reference films are spectra taken from the same region of the films as the sample film.

At 304, a background table having the reference background intensity spectra, each corresponding to a respective reference film thicknesses is generated. In one embodiment, the background table contains intensity spectra for the reference films as a function of thickness (or depth). The background table may contain other measurable values (thickness, dose . . . ) for the reference films that can be compared to the sample film.

At 306, thickness for the sample film is determined. The thickness of the sample film can be determined using various methods. An exemplary method of determining the thickness of the sample film is disclosed in U.S. patent application Ser. No. 11/118,035, entitled "Determining Layer Thickness Using Photoelectron Spectroscopy," which is hereby incorporated by reference in its entirety. It is to be anticipated that other methods suitable for film thickness determination can be used instead. The determined thickness of the sample film allows the film to be compared to the set of reference films that has the background energy signals measured as previously described. The thicknesses for the reference films are also determined using a similar method.

At 308, a background intensity spectrum is removed from the sample film. In comparing the measured intensity spectrum of the sample film to those in the background table, first, determine if the sample film has the same thickness as one of the reference films in the background table. Then, if the film thickness matches one of the reference films in the background table, the background intensity spectrum of that particular reference film (with the matching thickness) is used for the background subtraction from the sample film. If the film thickness is not already in the background table, a value is interpolated or reconstructed from the background table to derive the background intensity spectrum for the sample film. Thus, the background intensity spectrum to be subtracted from the sample film can be a reference background intensity spectrum already in the background table or a value interpolated or reconstructed using the background table.

It is to be appreciated that although thickness of a reference film and a sample film is one attribute used for the background spectrum interpolation, other suitable or convenient attributes of the films can be used. Examples of other suitable attributes include concentration, dose, deposition width, deposition condition, film formation, etc.

Figure 7:
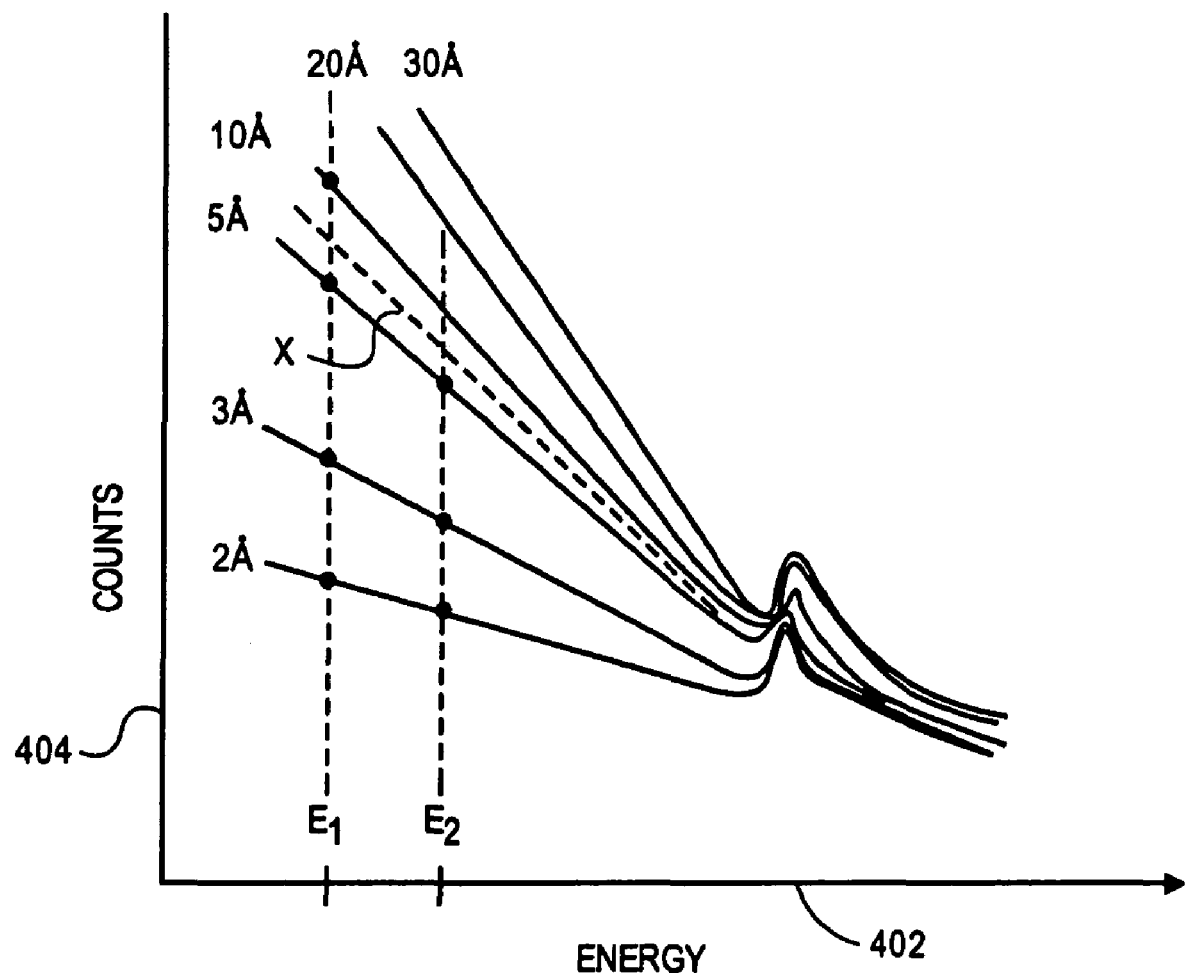
FIG. 7 illustrates an exemplary method of determining a background spectrum to be used for a sample film.

FIG. 7 pictorially illustrates an exemplary set of spectra for an exemplary set of reference films with their respective energy signals. It is to be understood that the spectra shown here are merely for illustrative purpose and the line shapes and the associated data may vary depending on the characteristics of the reference films. More or less number of spectra may be included and the exemplary spectra illustrated in this figure may represent only a small number actually implemented for a particular embodiment. In one embodiment, a spectrum is formed from a set of intensity readings or values obtained from a particular film.

In FIG. 7, the x-axis 402 represents the energy needed to excite electrons from the film or the kinetic energy of the electrons and the y-axis 404 represents the atom accounts or intensities of the electrons excited from the reference films and detected. The atom count or the intensities represent the energy signals for each film and are plotted against the energy. A sloped spectral line is generated for each reference film, in one embodiment. In this figure, the energy signals obtained for six (6) reference films are illustrated. The reference films have film thicknesses ranging from 2 Å-30 Å, which are only illustrative thicknesses. Other thicknesses may be included. For example, the energy spectral line at 2 Å indicates the signals for the reference film having a 2 Å thickness. As the reference film thickness increases, the count for the atoms increases. In this case, the slope of all lines will vary smoothly with thickness, therefore a slope value for an unknown thickness can be obtained by interpolation. For a sample film with a thickness X, for example, that falls between certain film thicknesses, e.g., between 5 Å and 10 Å, an a background spectra for the sample film is reconstructed interpolating the background spectra for the reference films of thicknesses, e.g., 5 Å and 10 Å. For instance, if the sample film has a thickness that falls between 5 Å and 10 Å, the constructed spectral energy line for the sample film is one that falls approximately between the spectral energy lines for the reference films with the thicknesses of 5 Å and 10 Å. The reconstructed spectral line for the sample film with the thickness X can be used for the background subtraction for the sample film.

Figure 8:
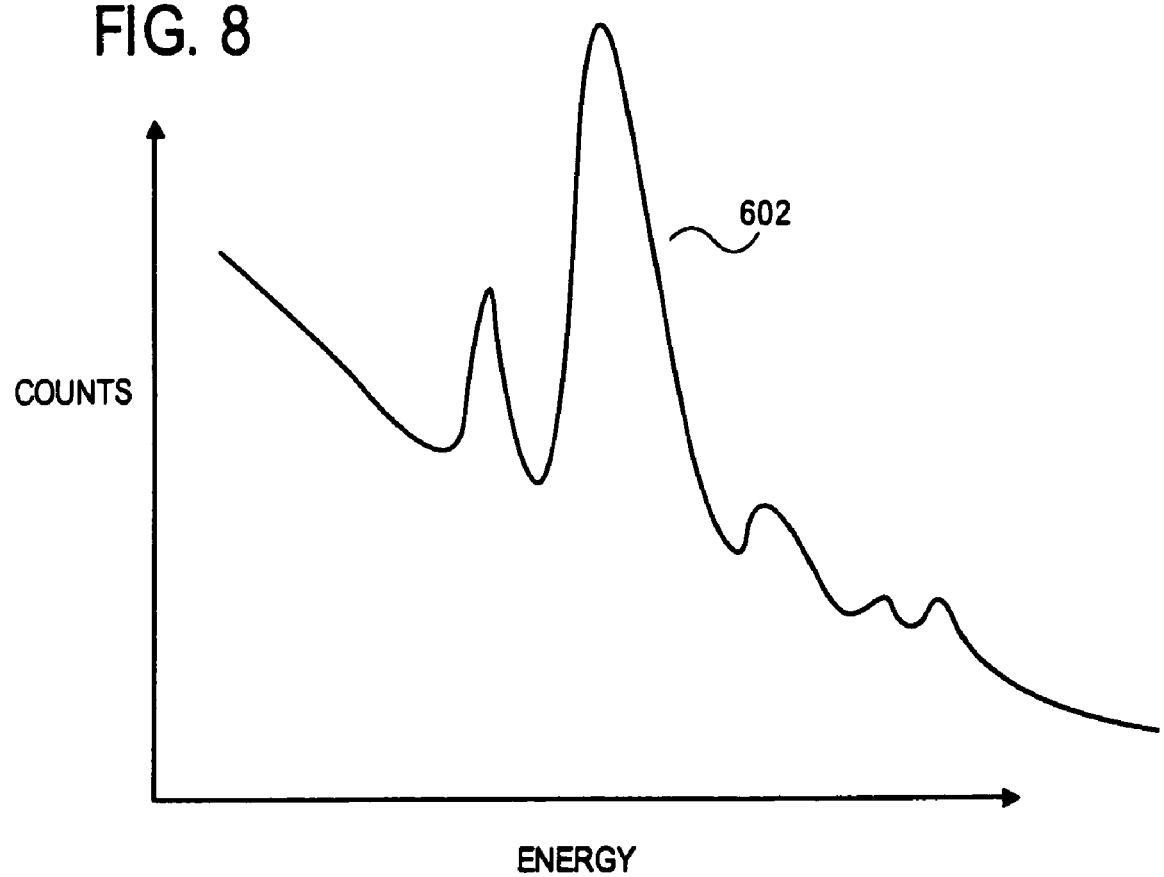
FIGS. 8-9 illustrate pictorially a background subtraction method.
Figure 9:
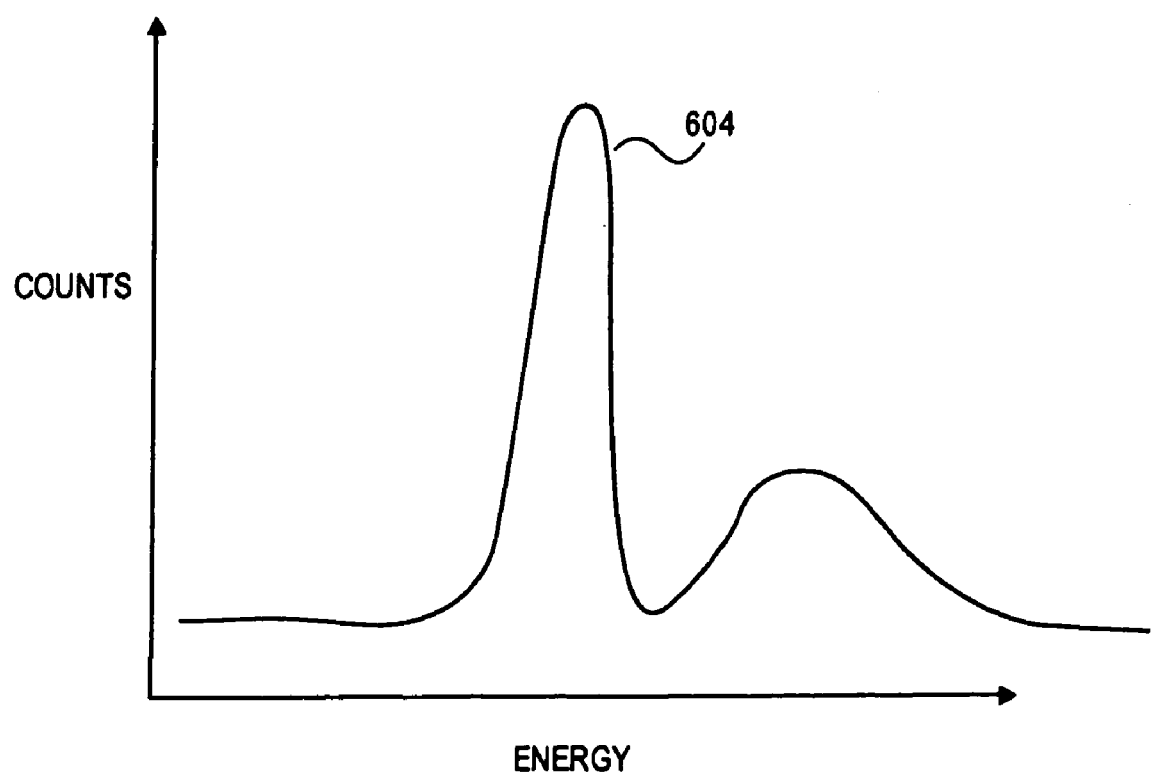

FIGS. 8-9 pictorially illustrate an exemplary background subtraction result for a sample film that contains SiON. In FIG. 8, spectral line 602 indicates a measured energy signal spectrum for the sample film that includes the background signal as well as the signal of the nitrogen element. In FIG. 9, the background signal is subtracted as previously discussed. Spectral line 604 represents the energy signals due to the nitrogen alone. As previously discussed, the background signal to be subtracted is determined by comparing the film thickness of the sample film to a set of film thicknesses of background reference films. The background signal for the sample film can either be a reference background intensity spectrum from the background table or a reconstructed background intensity spectrum using an interpolated value.

In one embodiment, the element of interest is nitrogen deposited in a silicon oxynitride (SiON) film. A large portion of the measured energy signals is in the regions of the N1s photoelectron signal and a large portion of the signals is due to inelastic scattered Si (Si2p and Si2s) photoelectron regions that originate from the SiON film (and from the underlying substrate). To simulate a set of reference background intensity values, in one embodiment, the N1s region is chosen. Measurements are taken for each reference film at the N1s energy region (in the absence of the nitrogen in the reference film) for each reference film, which is $SiO_2$ (since no nitrogen is present in the reference film). The measurements are then curve fitted to predict the shape of the spectral line for each reference film that is $SiO_2$ for a particular film thickness. The $SiO_2$ portion of the spectrum is referred to as a "generic background." The generic background contribution for an SiON film of a given measured thickness is considered to be identical to the fitted and extrapolated signal from an $SiO_2$ film of identical thickness. The difference between the measured N1s signal region on an SiON film and the corresponding generic background of the same SiO2 thickness is considered purely due to un-scattered and inelastic scattered nitrogen from the film. The fitting and prediction of the background region may also include other potential surface contaminant layers such as carbon, etc.

Figure 10:
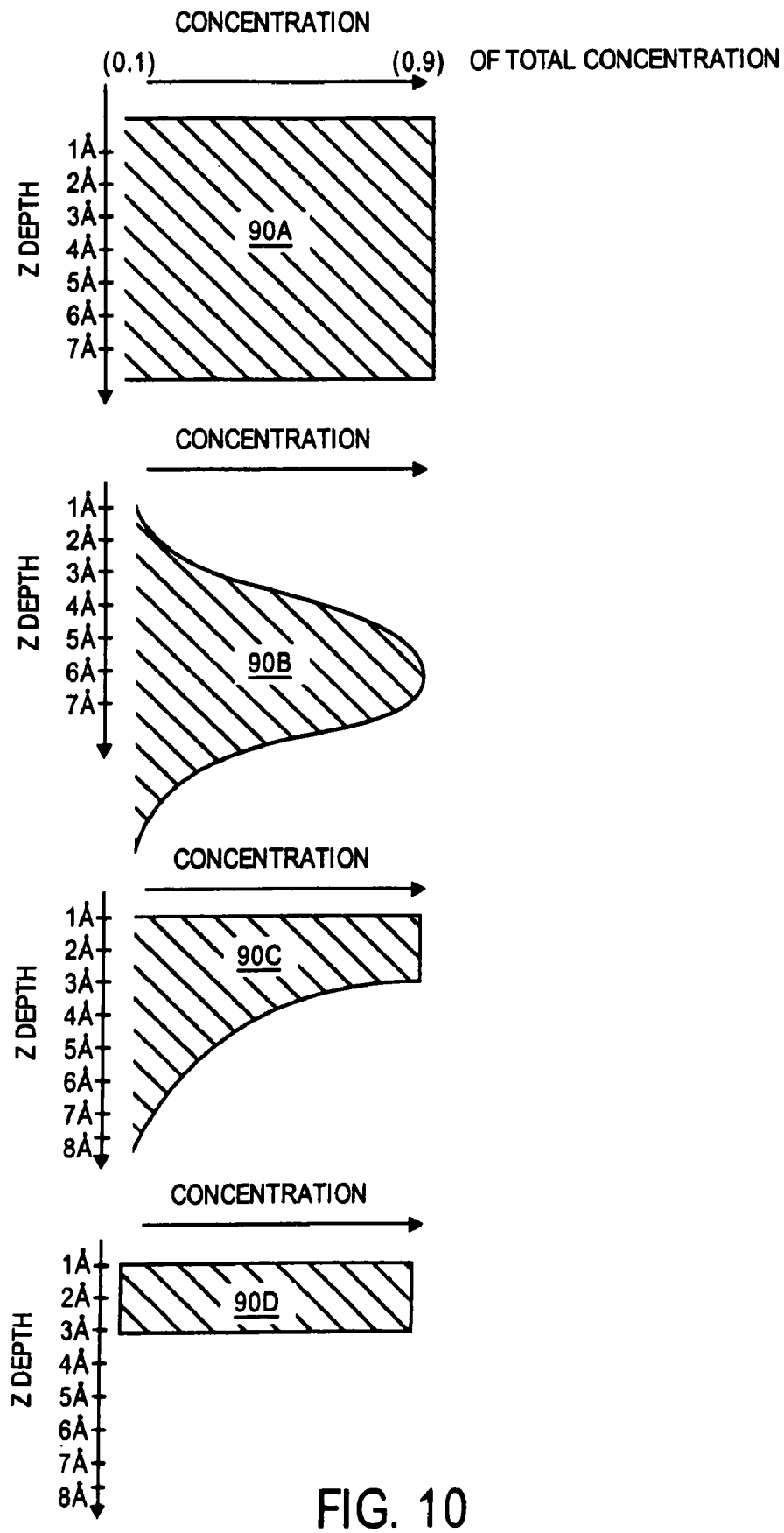
FIG. 10 illustrates exemplary possible distribution profiles.

FIG. 10 illustrates some examples of simulated distribution profiles for an element such as nitrogen in SiON. Simulated distribution profiles 90A, 90B, 90C, and 90D are provided. These simulated distribution profiles are provided for illustration purpose only and other profiles are entirely possible. Each of the distribution profiles 90A, 90B, 90C, and 90D has an associated energy spectrum. For each of the profiles 90A-90D, the distribution profile of the element has a concentration goes from 0.1 of the total concentration to 0.9 of the total concentration of the element deposited in a film. For each of the profiles 90A-90D, the depth of the element deposited goes from 1 Å-7 Å. The distribution profiles are stored for each of the profiles 90A-90D. The associated spectral line for each profile is also obtained. If the processed spectrum of the sample film (e.g., spectrum A) matches the spectral values of the profile 90A, then it can be expected that the sample film has the element distributed similarly to the profile 90A. If the processed spectrum of the sample film (e.g., spectrum A) matches the spectral values of the profile 90B, then it can be expected that the sample film has the element distributed similarly to the profile 90B. Various distribution profiles can be generated or simulated. The associated spectral lines are also determined and stored in a database. A process such as the process 800 can pull a particular distribution profile form the database and perform the comparison as previously described. In one embodiment, selecting a particular distribution profile to compare to the processed spectrum is automated and/or continuous until a match is found for the processed spectrum.

Figure 11:
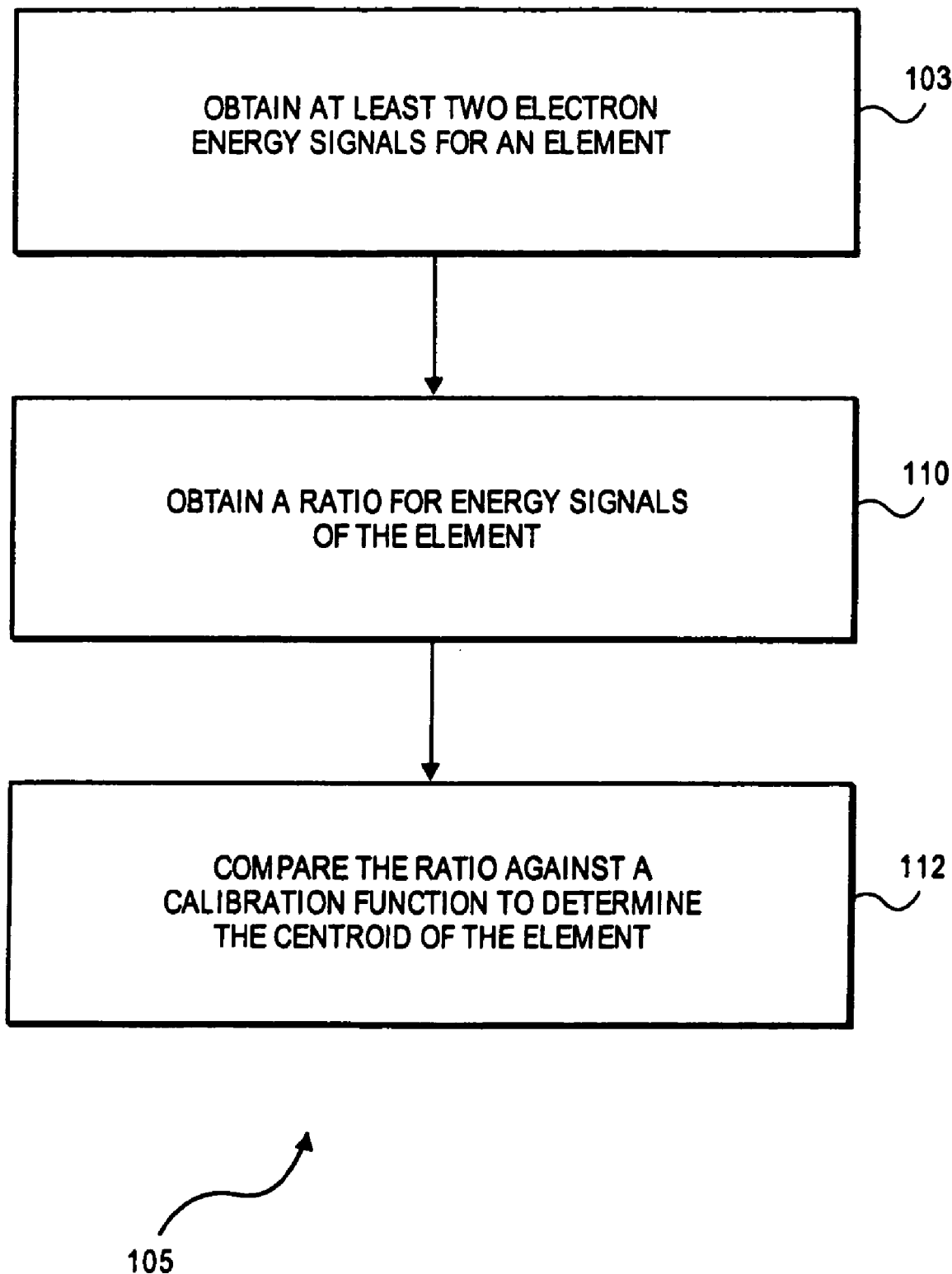
FIGS. 11-12 illustrate an exemplary method of determining a centroid value for an element in a film using intensities' ratio.

FIG. 11 illustrates a characterization process 105 that utilizes a ratio of signal intensities of the same elements. In one embodiment of the process 105, electron energy signals are obtained for the element in the thin sample film at 103. A ratio for the measured energy signals of the element is obtained at 110. At least two different electron species from the same element are obtained. The analysis of the sample film involves the use of the measured energy signals for the element derived from two or more different electron species of the same element. In one example, the element is nitrogen and the sample film is a silicon oxynitride film. Two different characteristic electrons for the nitrogen element are emitted and each having different kinetic energy from the other. In one embodiment, one electron emitted is from the N1s orbital of the nitrogen atom called "N1s energy signal" and the other electron emitted is from the NKLL (Auger region) of the nitrogen atom called "NKLL energy signal." In one embodiment, the ratio of the two measured energy signals of the element is indicative of the centroid of the element in the film. At 112, the energy signal ratio is compared against a calibration function to determine the distribution profile for the element in the sample film.

Figure 12:
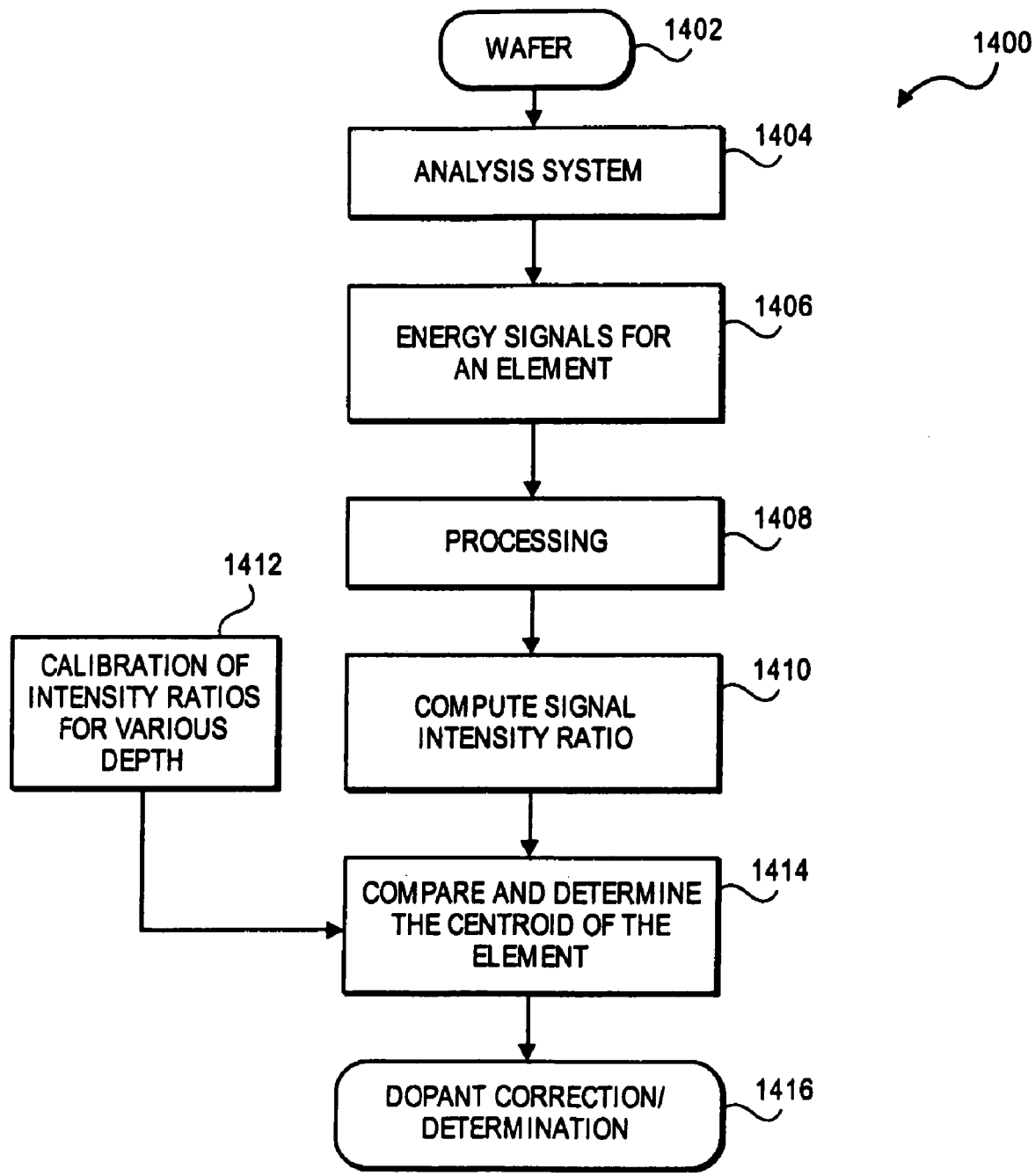

FIG. 12 illustrates an exemplary method 1400 of determining a centroid of an element (e.g., nitrogen) in a film (e.g., SiON). In the method 1400, the ratios of two different energy signals for the same elemental species are used for this analysis. In one embodiment, the element of interest is nitrogen. In the present embodiment, the energy signals for nitrogen at the N1s region and the NKLL (Auger) region are used for the analysis. Other energy signals can also be used without exceeding the scope of the invention.

At 1402, a wafer is provided. The wafer contains the sample film with the element to be analyzed. For instance, the wafer is a semiconductor substrate with the film SiON formed thereon and the element nitrogen is to be analyzed. The wafer is placed into an analysis system at 1404, e.g., XPS, previously described. At 1406, two energy signals are obtained for the nitrogen in the SiON film. At 1408, the energy signals are processed. The energy signals are processed to remove any background noises or other information not pertaining to the signals from the energies excited from the sample film. At 1410, a signal intensity ratio is computed for the element. The signal intensity for the nitrogen at the N1s region is expressed as "I(N1s)" and the signal intensity for the nitrogen at the NKLL region is expressed as "I(NKLL)." The ratio for the signal intensities is expressed as R(sample). The ratio R(sample) can be expressed as $$R(sample) = I(N1s)/I(NKLL) \quad (1)$$

The ratio of the energy signals at the N1s species and the NKLL species are useful for centroid determination at least for the following reasons. The two different energy signals attenuate differently as they traverse the SiON film. For instance, the attenuation of the energy signal from the N1s species is much less compared to the attenuation of the energy signal from the NKLL species. One reason for that is that, originating from a particular depth, the N1s species is emitted at higher kinetic energy compared to the NKLL species and thus, the signal will attenuate less compared to the energy for the NKLL species, which has lower emission energy. The ratio of the energy signals from the N1s and NKLL regions vary as the depth of the nitrogen element varies. Thus, the dependence of the ratio of the signal intensities on the centroid location is expressed as:

$$I(N1s)/I(NKLL) \sim e^{tc/\lambda(N1s)}/e^{-tc/\lambda(NKLL)} \quad (2)$$

Where "tc" stands for the centroid value of the element and "λ" stands for the attenuation length of the element at a particular region. Thus, λ(N1s) stands for the attenuation length of the nitrogen from the N1s species and λ(NKLL) stands for the attenuation length of the nitrogen from the NKLL species. The attenuation length values are know or can be determined.

Figure 13:
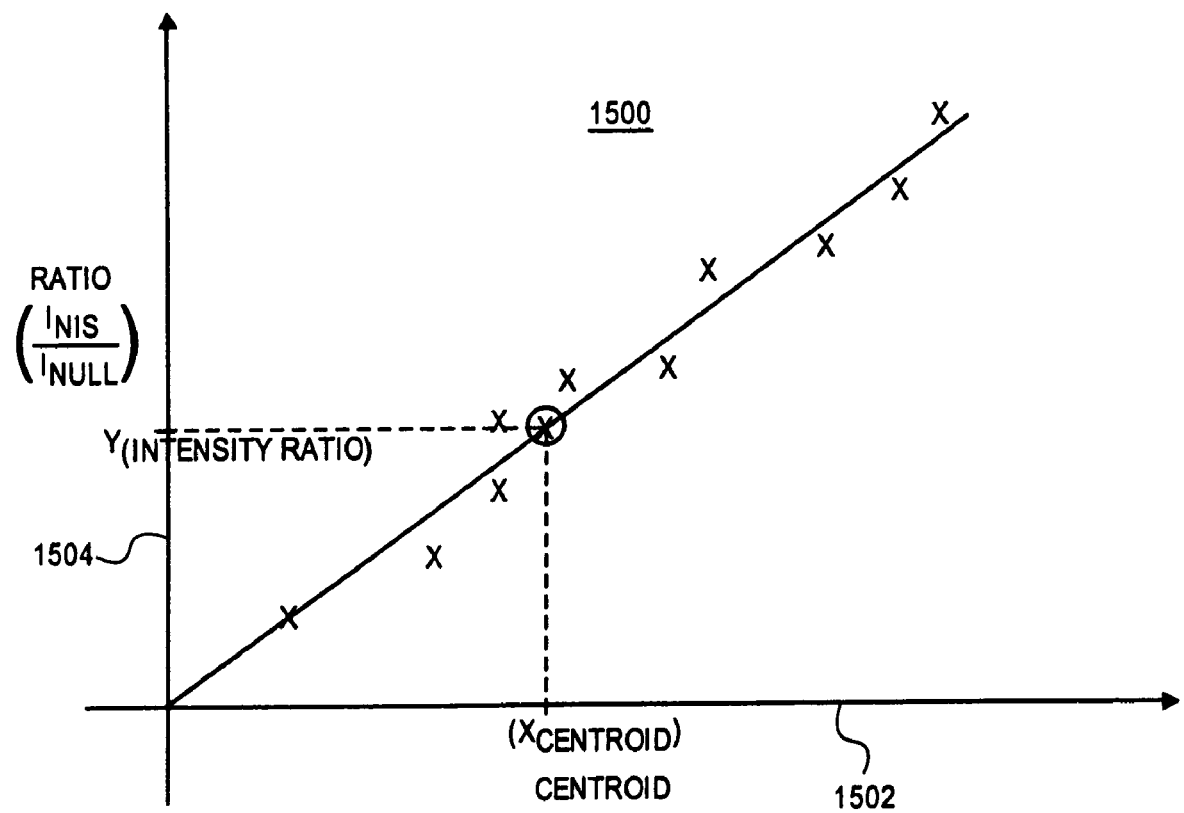
FIG. 13 illustrates a calibration curve that can be used in a method of determining a centroid value of a distribution profile of an element in a sample film using signal intensity ratios.

The ratios thus allows for the extraction of the centroid of the element in the sample film. It is to be anticipated that the energy signals at other regions for an element can be used. In one embodiment, to determine the centroid of nitrogen in the SiON film, a calibration function is provided. At 1412, a set of intensity ratios for nitrogen at various known centroid values in the SiON film is provided. The ratios for the signal intensities for nitrogen deposited with various centroids are obtained. The ratio of the signal intensities varies according to the centroid of the depth distribution of the element in the film as illustrated in FIG. 13. At 1414, the signal intensity ratio of the element is compared to the set of intensity ratios for nitrogen at various depths to determine the centroid of nitrogen in the sample film At 1416, dopant correction and/or determination of nitrogen in the sample film are performed. In the embodiments where XPS or Auger spectroscopy is used, often only about 10 nm of the surface of the sample film is measured. The mean depth of the distribution of the element in the sample film may introduce some interpretation errors in the reported atomic concentration or dose of a film constituent. If the mean depth of a film dopant (element deposition) is at the surface, no attenuation of the measured signal has to be taken into account. On the other hand, if the mean depth (the centroid) of the element of the same number of atoms is, for example, at 3 nm and the electron attenuation length λ is 3 nm, only a fraction of the emitted electron signal ($e^{-tc/\lambda}$) will be detected. In order to improve the accuracy of a reported dose or atomic concentration result, the measured signal intensity of the element of interest would have to be corrected by a factor $1/e^{(-tc/\lambda)}$.

In order to correct the standard XPS dose determination made assuming a uniform depth distribution for the element of interest a correction factor of $$\frac{e^{\frac{T}{2\lambda(E(Si2p))_{SiO2}}}}{e^{\frac{C}{\lambda(E(N1s))_{SiO2}}}}$$

is used. In the correction factor, T=thickness of the film, $\lambda(E(Si2p))_{SiO2}$=attenuation length of the Si 2p species in SiO2, and $\lambda(E(N1s))_{SiO2}$=attenuation length of the N1s species in SiO2.

FIG. 13 illustrates an exemplary calibration graph 1500. The x-axis represents the centroid values and the y-axis represents the ratio values for the signal intensities. The ratio values are plotted against the associated centroid values. The centroid values for the intensity ratios can be determined using the equation (2) above. A calibration function can also be obtained, for example, a linear regression function. For example, a calibration function for the graph 1500 can be expressed as y=mx+b; where "m" is the slope of the line and "b" is the y-intercept. For a particular sample film, once the intensity ratio is determined as described above, the centroid value can be obtained from the linear equation as centroid=x=(y-b)/m.

An other embodiment of the present invention pertain to a method to isolate the signal emitted by a first species (signal spectrum) from the signals emitted by different species (background spectra) whose initial emission kinetic energy is larger than the kinetic energy of the first species. The photoelectrons emitted by the different species will lose energy through inelastic scattering and will be detected in the same energy range as the photoelectrons from the first species. The detected spectrum is the sum of the background spectrum and the signal spectrum. One method to subtract the background spectrum from the measured spectra is to obtain an independent measurement of the background spectrum, i.e. by collecting a photoelectron spectra on a sample (background sample) with the same bulk/surface property of the sample of interest that doesn't contain the element to be analyzed.

Often it is difficult to prepare such a background sample. One embodiment of the present invention pertains to a method of reconstructing the background spectrum from prime principles using electron transport theory. Most of the background elements of which the bulk is composed have known (or uniform depth distribution), therefore, given the intrinsic spectra for each of the species at high emission kinetic energy the full background spectra can be reconstructed, normalized and subtracted to isolate the spectra of the photoelectrons emitted by the species with unknown depth distribution.

Figure 14:
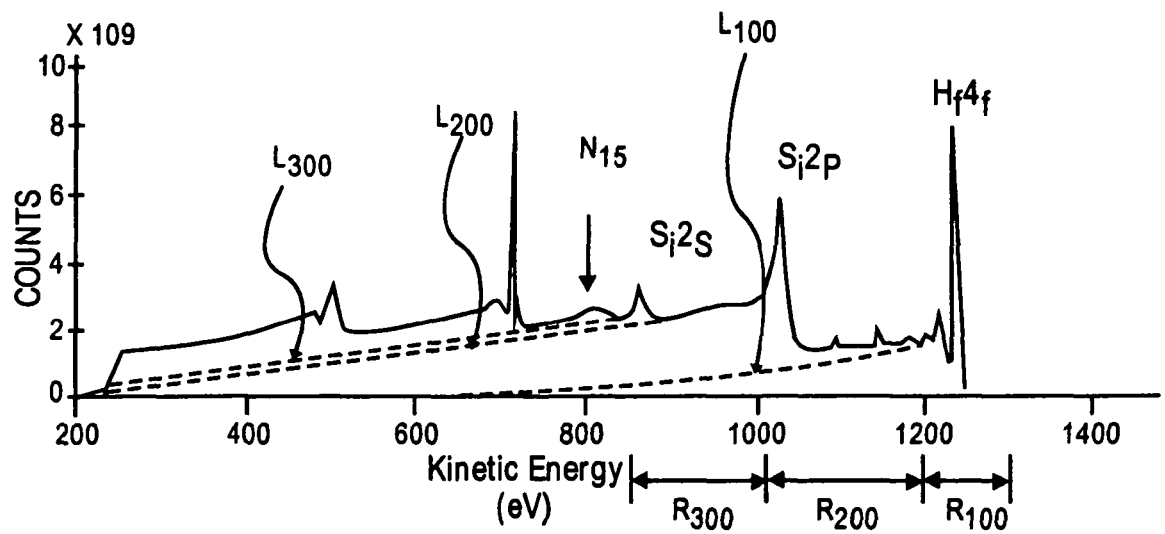
FIG. 14 illustrates an exemplary spectrum having multiple electron signals representing multiple elements in a film.

For instance, referring to FIG. 14, a film may include hafnium (Hf), silicon (Si), and nitrogen (N). In one case, nitrogen is the element of interest. In one example, for a total spectrum of the film, a peak at about 1250 KE is that of $Hf_{4f}$ from hafnium, another peak at about 1050 KE is that of $Si_{2p}$ from silicon, another peak at about 850 KE is that of $Si_{2s}$ from silicon, and at about 800 is an N1s from nitrogen. As illustrated here, the spectral lines (or spectra) from $Hf_{4f}$ from hafnium, and $Si_{2p}$ and $Si_{2s}$ from silicon contribute to the background of the spectral line (spectrum) for the nitrogen $N_{1s}$. Thus, to analyze or isolate the signals form the $N_{1s}$ region only, the spectra particular to $Hf_{4f}$, $Si_{2p}$, and $Si_{2s}$ need to be removed. In the absence of an appropriate reference film the background spectral line(s) can be simulated using one or more exemplary methods of the present invention.

FIG. 15 illustrates an exemplary method 2200 which illustrate a method of analyzing one or more elements in a film such as the film similar to the film shown in FIG. 14. One or more elements in a film can be the background materials for another element in the film. In method 2200, one element's spectrum is obtained first and then used as the background spectrum for another element. In one embodiment, the species that exhibits the highest kinetic energy (KE) is analyzed first and used as a background for the spectra associated with all the other lower emission kinetic energy species. In the example shown in FIG. 14, the $Hf_{4f}$ spectrum will be analyzed and reconstructed first. Being the highest emission kinetic energy species its background is just residual radiation that can be approximated with a linear fit. A subregion of the spectra containing solely the $Hf_{4f}$ spectral region is selected and used to determine the $Hf_{4f}$ depth distribution as described previously in the N1s example. The step of determining the $Hf_{4f}$ spectrum depth distribution can be skipped if it is known already—as in the case where the $Hf_{4f}$ spectrum is part of the bulk uniform material. Given the $Hf_{4f}$ depth distribution a simulated spectrum can be generated over the whole energy range collected in the measured spectrum and after proper normalization subtracted. The subtracted spectrum now will be the superposition of the spectra of the remaining species, in this example the N1s, $Si_{2p}$ and $Si_{2s}$. The same process can be repeated for the next highest emission kinetic energy species.

Alternatively the depth distribution of each of the species can be found simultaneously with optimization method similar to the one explained in the N1s example by minimizing the difference between the full measured spectrum and a simulated spectrum that is given by the superposition of the spectra simulated for each of the species. Since the full spectrum is analyzed, beginning from the highest emission kinetic energy species, there is no need to subtract the background spectra from species at higher emission kinetic energy.

Figure 16:
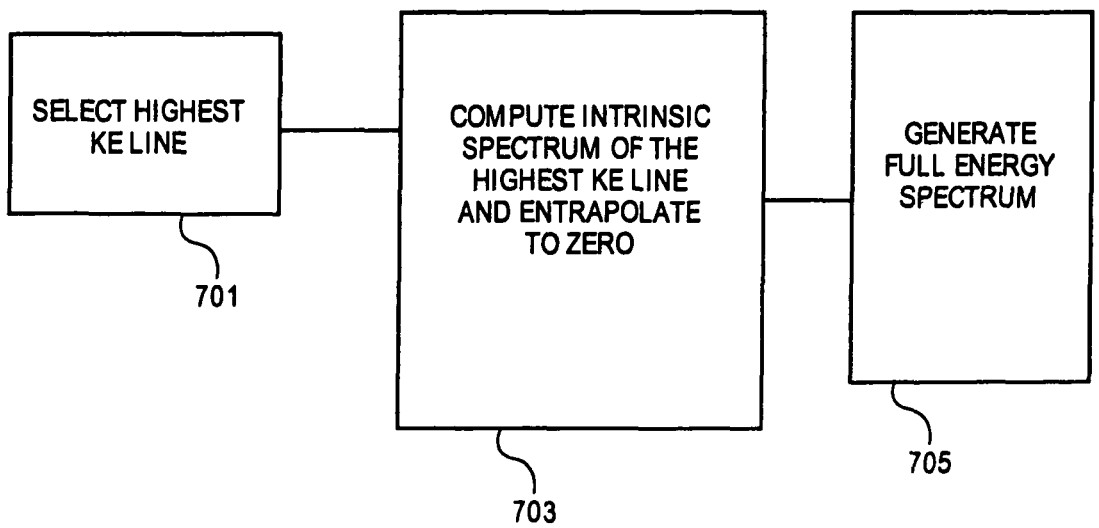

In order to carry out the full spectral analysis it is required to determine the intrinsic for each of the species present in the spectrum under analysis. In order to do a set of reference wafers for which the depth distribution of all species is known is needed. For example a bare Si wafer can be used to extract the Si metal intrinsic spectrum, a pure HfO2 wafer can be used to determine the Hf4f Hf4d, Hf4p intrinsic and O2s, O1 s and so on . . . . Referring to FIG. 16, for each reference wafer, at 701, the energy region containing solely the spectrum of the highest emission kinetic energy line is selected. At 703, the intrinsic spectrum for that species is computed over that energy range and linearly extrapolated to zero at the lower energy. At 705, the full energy range spectrum is generated using the intrinsic spectrum found at 703 and the known depth distribution for that element. At 707, the reconstructed spectrum is subtracted from the measured spectra obtaining a background subtracted spectrum for the next species. The same procedure is repeated on the background subtracted spectrum for the next highest kinetic energy species.

The intrinsic spectra found analyzing the reference wafers with the embodiment described in FIG. 16 can be used to determine the unknown depth distribution of one or more elements in the sample film as previously described. The process of generating a simulated spectrum or simulated spectra in real time during regression can be time consuming. In order to overcome this difficulty one can pre-compute PI coefficients for each spectrum and use the PI coefficients to reconstruct the spectrum.

In one embodiment, a method is provided to simulate, in real time, a modeled spectrum with a known distribution profile. The PI coefficients characteristic of the depth distribution of a given species and the scattering process (elastic and inelastic) are pre-computed, for example, using a Monte Carlo or other suitable methods. The PI coefficients are pre-computed for a sparse set of depth distributions and stored in a PI coefficients database. Such set of PI coefficients can be organized in the database as a function of parameters defining the associated depth distributions. During real time simulation of the spectrum associated to an arbitrary depth distribution the appropriate PI can be found by interpolating the pre-computed PI in the space of parameters describing the depth distribution. The interpolated PI coefficients are than used to reconstruct the spectrum to be used as a simulated spectrum (for example a background spectrum or a signal spectrum pertaining to the element of interest) or to reconstruct the scattering contribution to be subtracted from a processed spectrum (as previously discussed) to obtain an intrinsic spectrum. The same type of interpolation scheme can be done if the full spectra associated to the sparse set of depth distribution is stored, but that would require a much larger storage memory for the database.

Embodiments of the present invention are particularly advantageous in characterization of certain oxide layers. For example, such oxide layers may include silicon oxide layers, oxynitride films, nitrided oxide layers, silicon oxynitride (ONO) films, etc. For example, such oxide layers may be formed as thin films having thicknesses less than about 10 nanometers, and even 2 nanometers, and used for gate oxides in the fabrication of semiconductor devices such as field effect transistors (FET). Such transistors are used in various integrated circuit devices including processing devices, memory devices, etc. Further, the present invention is advantageous in measuring the shape and dose of thin implant regions with accurate quantitative results and chemical composition information. For example, a silicon substrate may be implanted with $BF_2$ in the formation of semiconductor devices. The present invention may be used to characterize such a formed implanted thin layer or region by depth profiling the implanted silicon substrate sample.

Figure 17:
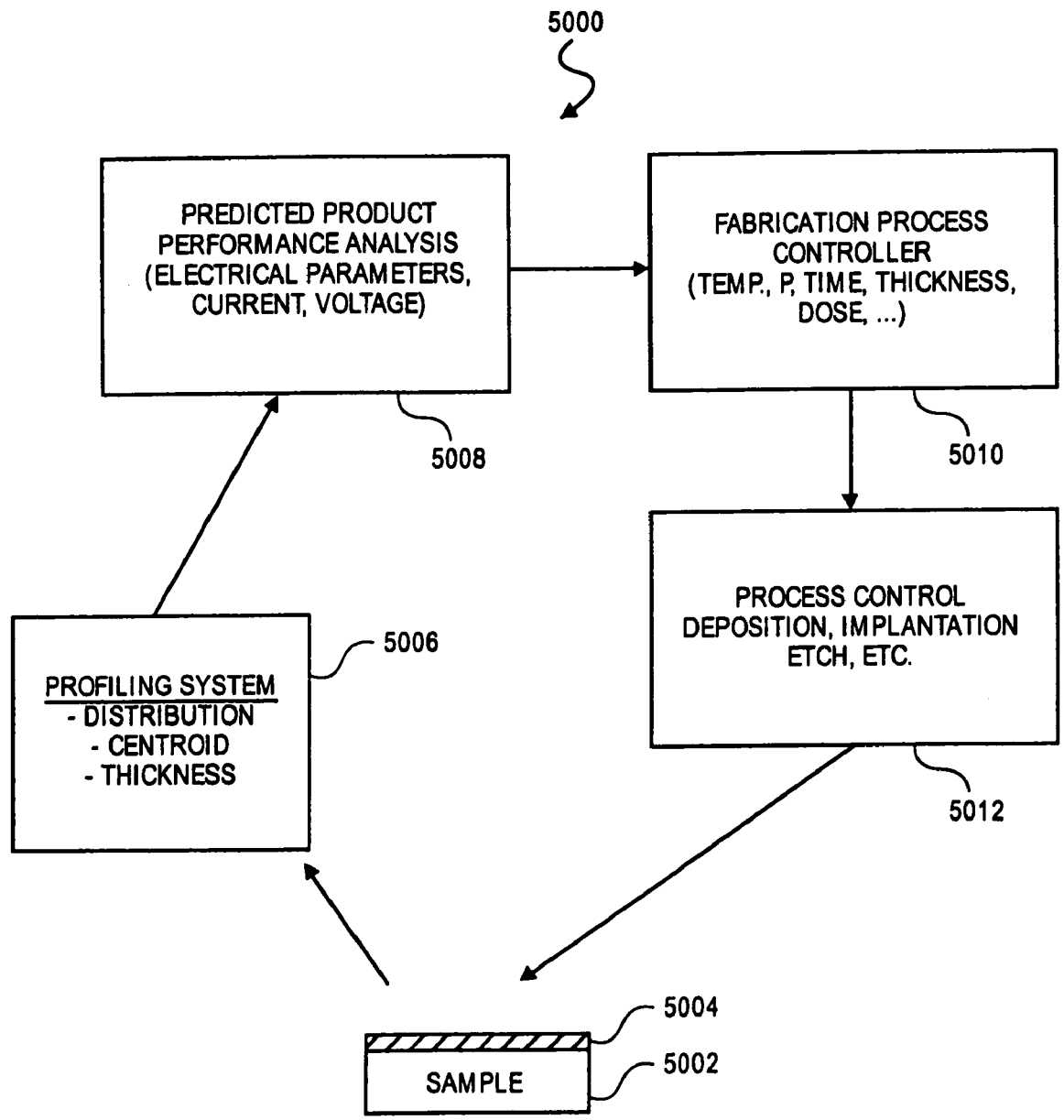
FIGS. 17-18 illustrate exemplary processes according to one or more embodiments of the present invention.

Additionally, embodiments of the present invention can be used in predicting electrical performances or parameters of devices that are formed in or on the sample film as previously described. FIG. 17 illustrates an exemplary process 5000 of using predicted electrical product performance using distribution profile, thickness, and/or centroid value of an element in a sample film 5004. The sample film 5004 may be formed on a substrate sample 5002 such as a wafer. The distribution profile, thickness, and centroid value of the element in the sample film 5004 can be determined as previously described. In one embodiment, the sample film 5004 is put through a profiling system 5006 for the distribution profile, thickness, and centroid value determination as previously described. The values obtained from the profiling systems 5006 are then passed to a predict product performance analysis system 5008. Here, the distribution profile of the element, centroid value of the element, and the film thickness are then used to predict electrical parameters for devices that are to be formed in or on the sample film. For instance, drive current and threshold voltage of a device can be predicted using the centroid value for the element to yield "predicted electrical parameters." The predicted electrical parameters can then be fed into a fabrication process controller 5010 so that process parameters can be controlled, monitored, and/or modified accordingly or according to desired product performance. For instance, the temperature, pressure, time, thickness, dose, etc. . . . for forming the sample film can be monitored and/or modified to achieve a desirable result using a centroid/thickness value. Additionally, a dimensionless value such as centroid/thickness can be used to correlate to a particular electrical parameter. Thus, an electrical parameter of a film can be predicted, monitored, controlled, or modified using the results obtained from the profiling system. The fabrication process controller 5010 can use the information to control other processes (box 5012) in a system, such as controller the deposition, implantation, or etching processes that are used in device fabrication.

Figure 18:
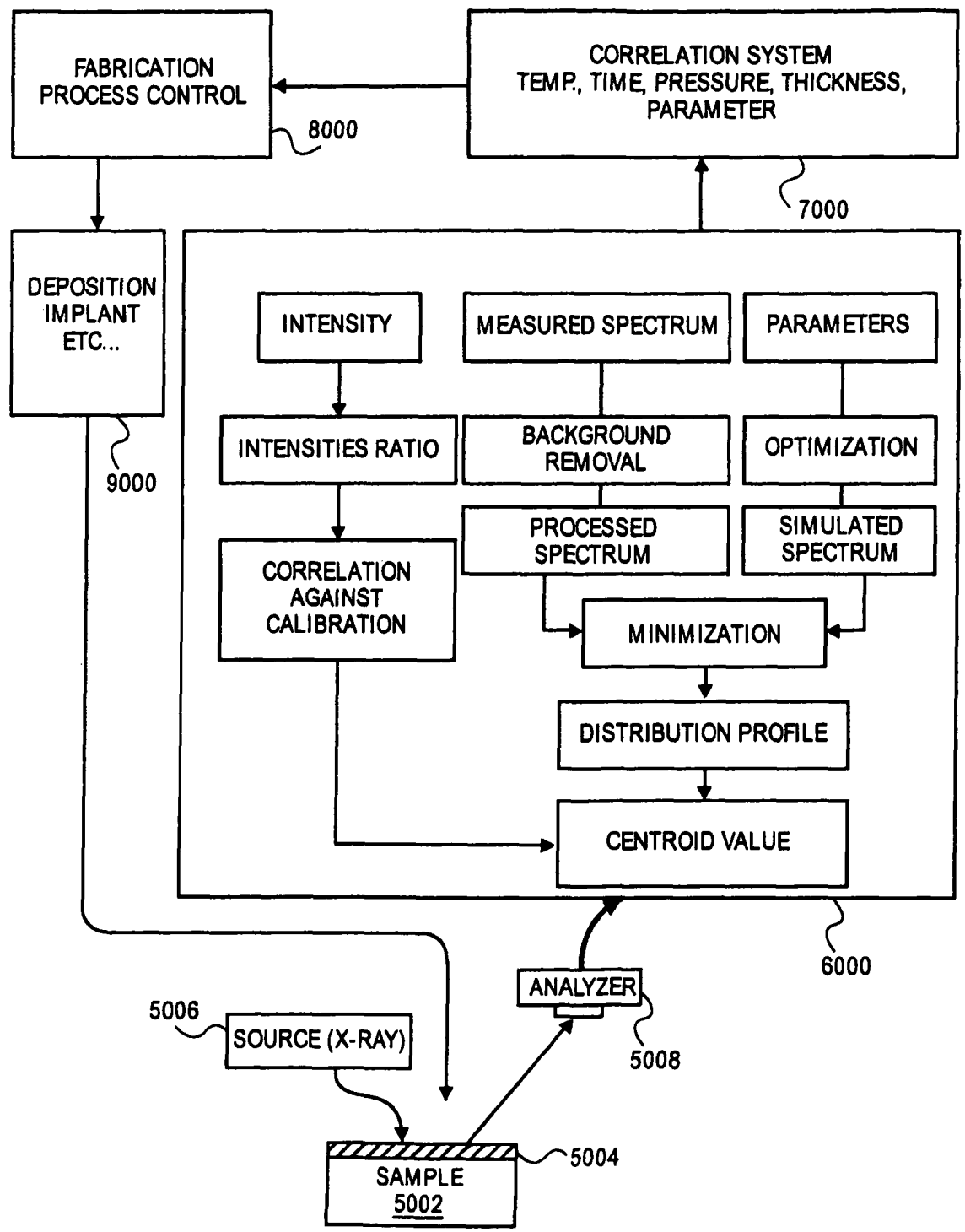

FIG. 18 illustrates an exemplary process 5001 of using predicted electrical product performance using distribution profile, thickness, and/or centroid value of an element in a sample film 5004. As before, the sample film 5004 may be formed on a substrate sample 5002 such as a wafer. The distribution profile, thickness, and centroid value of the element in the sample film 5004 can be determined as previously described. In one embodiment, a photoelectron system such as an XPS system with an X-ray source 5006 is used to excite photoelectron(s) from the sample film 5004 for analysis are previously described. An analyzer 5008 is used to analyze the sample film 5004 as previously described. The data are then put through a profiling system 6000 for analysis such as distribution profile, thickness, and centroid value determination as previously described.

In the profiling system 6000, analysis such as intensity ratios determination, distribution profile and centroid value determination are performed as previously described. In one embodiment, signal intensities for an element are obtained and an intensity ratio is generated. The ratio is correlated against a calibration function to determine a centroid value for the element as previously described. In another embodiment, a measured spectrum for an element is obtained. A background subtraction is performed using any one of the methods previously described to obtain a processed spectrum. Minimization and optimization (using appropriate parameters to simulate a simulated spectrum) are then performed to determine a distribution profile for the element using methods previously described. A centroid value can also be derived.

The values obtained from the profiling systems 6000 are then passed to a predict product correlation system 7000. Here, the values are correlated to parameters such as temperature, time, pressure, thickness, and electrical parameters. The distribution profile of the element, centroid value of the element, and the film thickness can be then used to predict electrical parameters for devices that are to be formed in or on the sample film as previously discussed. For instance, drive current and threshold voltage of a device can be predicted using the centroid value for the element to yield predicted electrical parameters. The predicted electrical parameters can then be fed into a fabrication process controller 8000 so that process parameters can be controlled, monitored, and/or modified accordingly or according to desired product performance. For instance, the temperature, pressure, time, thickness, dose, etc. . . . for forming the sample film can be monitored and/or modified to achieve a desirable result using a centroid/thickness value. Additionally, a dimensionless value such as centroid/thickness can be used to correlate to a particular electrical parameter. Thus, an electrical parameter of a film can be predicted, monitored, controlled, or modified using the results obtained from the profiling system. The fabrication process controller 8000 can use the information to control other processes (box 9000) in a system, such as controller the deposition, implantation, or etching processes that are used in device fabrication.

As one skilled in the art will recognize from the description above, the sample may take one of many different forms. For example, the sample may be a layer formed on a substrate or a region formed within a substrate, as well as any other sample formed of a material that would benefit from being characterized according to the present invention. As such, the present invention is not to be taken as limited to any particular material or structure listed herein. However, the present invention does have particular advantages in characterizing certain thin films, e.g., gate dielectric layers such as gate oxide layers.

While the invention has been described in terms of several embodiments, those of ordinary skill in the art will recognize that the invention is not limited to the embodiments described. The method and apparatus of the invention, but can be practiced with modification and alteration within the spirit and scope of the appended claims. The description is thus to be regarded as illustrative instead of limiting.

Having disclosed exemplary embodiments, modifications and variations may be made to the disclosed embodiments while remaining within the spirit and scope of the invention as defined by the appended claims.

The invention claimed is:
1. A method comprising:
exciting at least two electron energies of an element deposited in a sample film;
obtaining an intensity ratio value for said electron energies, said intensity ratio value comprising a first intensity value and a second intensity value associated with said electron energies, said first intensity value and said second intensity value representing a first electron energy value and a second electron energy value for said element;

correlating said intensity ratio value to a correlation function associating with a set of intensity ratio values as a function of centroid of the element in a reference film, said reference film being comparable to said sample film; and determining a centroid of said element in said sample film based on said correlating.

2. The method of claim 1, wherein further comprising:

obtaining said set of intensity ratio values for said element by exciting said two electron energies from said element deposited in each of said reference film with a known centroid value; and generating said intensity ratio values for said element as a function of centroids.

3. The method of claim 2, further comprising:

determining a centroid value for said element in said sample film.

4. The method of claim 3, further comprising at least one of:

determining a dose level for said element in said sample film;

correcting a dose level for said element in said sample film;

predicting an electrical parameter for a device to be formed in or on said sample film; and controlling an electrical parameter for a device to be formed in or on said sample film using said centroid value for said element in said sample film.

* * * * *